United States Patent
Kawashima et al.

(10) Patent No.: US 9,121,829 B2
(45) Date of Patent: Sep. 1, 2015

(54) CRYSTALLINITY EVALUATION METHOD, CRYSTALLINITY EVALUATION DEVICE, AND COMPUTER SOFTWARE THEREOF

(71) Applicants: PANASONIC CORPORATION, Osaka (JP); PANASONIC LIQUID CRYSTAL DISPLAY CO., LTD., Hyogo (JP)

(72) Inventors: Takahiro Kawashima, Osaka (JP); Genshiro Kawachi, Chiba (JP); Tomohiko Oda, Osaka (JP); Hikaru Nishitani, Nara (JP)

(73) Assignees: JOLED INC., Tokyo (JP); PANASONIC LIQUID CRYSTAL DISPLAY CO., LTD., Hyogo (JP)

( * ) Notice: Subject to any disclaimer, the term of this patent is extended or adjusted under 35 U.S.C. 154(b) by 452 days.

(21) Appl. No.: 13/645,621

(22) Filed: Oct. 5, 2012

(65) Prior Publication Data

US 2013/0030728 A1 Jan. 31, 2013

Related U.S. Application Data

(63) Continuation of application No. PCT/JP2012/000752, filed on Feb. 3, 2012.

(30) Foreign Application Priority Data

| Mar. 4, 2011 | (JP) | ................................. 2011-048369 |
| Oct. 12, 2011 | (JP) | ................................. 2011-225375 |

(51) Int. Cl.
- *G01N 21/65* (2006.01)
- *H01L 21/66* (2006.01)
- (Continued)

(52) U.S. Cl.
CPC ................ *G01N 21/65* (2013.01); *H01L 22/12* (2013.01); *H01L 29/66765* (2013.01); *C30B 33/00* (2013.01); *H01L 2924/0002* (2013.01)

(58) Field of Classification Search
USPC .................................................. 702/56, 183
See application file for complete search history.

(56) References Cited

U.S. PATENT DOCUMENTS

| 5,795,795 A | 8/1998 | Kousai et al. |
| 6,143,661 A | 11/2000 | Kousai et al. |
| (Continued) | | |

FOREIGN PATENT DOCUMENTS

| EP | 0473988 | 3/1992 |
| JP | 61-153277 | 7/1986 |
| (Continued) | | |

OTHER PUBLICATIONS

U.S. Appl. No. 13/451,078 to Tomohiko Oda et al., filed Apr. 19, 2012.

(Continued)

*Primary Examiner* — Mohamed Charioui
(74) *Attorney, Agent, or Firm* — Greenblum & Bernstein, P.L.C.

(57) ABSTRACT

A crystallinity evaluation method of evaluating crystallinity of a semiconductor film formed above a substrate includes following steps. First, a peak waveform of a Raman band in a Raman spectrum of the semiconductor film is obtained using Raman spectrometry. The Raman band corresponds to a phonon mode unique to the semiconductor film. The peak waveform is a wavelength range having a peak of the Raman band. Next, a first waveform is generated by fitting the obtained peak waveform by Gauss function. Then, a peak value of the first waveform is extracted. Then, a second waveform is generated by fitting the obtained peak waveform by Lorenz function based on the extracted peak value. Then, a peak value, a FWHM, and/or a wavelength indicating the peak value regarding the generated second waveform are obtained. Then, crystallinity of the semiconductor film is evaluated based on the obtained information.

19 Claims, 22 Drawing Sheets

(51) Int. Cl.
*H01L 29/66* (2006.01)
*C30B 33/00* (2006.01)

(56) References Cited

U.S. PATENT DOCUMENTS

| | | | |
|---|---|---|---|
| 6,559,036 | B1 | 5/2003 | Ohtani et al. |
| 7,186,600 | B2 | 3/2007 | Ohtani et al. |
| 7,847,294 | B2 | 12/2010 | Ohtani et al. |
| 2002/0013114 | A1 | 1/2002 | Ohtani et al. |
| 2006/0113891 | A1* | 6/2006 | Nishimura et al. ........... 313/496 |
| 2007/0117293 | A1 | 5/2007 | Ohtani et al. |
| 2007/0141347 | A1* | 6/2007 | Nakagawa et al. ........... 428/408 |
| 2011/0146756 | A1 | 6/2011 | Sasaki et al. |
| 2011/0318891 | A1 | 12/2011 | Oda et al. |
| 2012/0032179 | A1 | 2/2012 | Saitoh et al. |
| 2012/0211758 | A1 | 8/2012 | Sugawara |

FOREIGN PATENT DOCUMENTS

| | | |
|---|---|---|
| JP | 3-109719 | 5/1991 |
| JP | 4-179118 | 6/1992 |
| JP | 4-296015 | 10/1992 |
| JP | 6-342909 | 12/1994 |
| JP | 08-148428 | 6/1996 |
| JP | 10-107106 | 4/1998 |
| JP | 2000-114527 | 4/2000 |
| JP | 3305592 | 7/2002 |
| JP | 3535241 | 3/2004 |
| JP | 2004-109032 | 4/2004 |
| WO | 2010/024211 | 3/2010 |
| WO | 2010/101066 | 9/2010 |

OTHER PUBLICATIONS

U.S. Appl. No. 13/425,879 to Hiroshi Hayashi et al., filed Mar. 21, 2012.
U.S. Appl. No. 13/338,816 to Yuta Sugawara, filed Dec. 28, 2011.
International Search Report in PCT/JP2012/000752, dated Apr. 10, 2012.
Qi Wang et al., "Raman study of films of amorphous-to-microcrystalline silicon prepared by hot-wire chemical vapor desposition", Journal of Applied Physics, vol. 94, No. 5, pp. 2930-2936 (Sep. 1, 2003).

* cited by examiner (a) Stokes Light  (b) Rayleigh Light  (c) Anti-Stokes Light

CRYSTALLINITY EVALUATION METHOD, CRYSTALLINITY EVALUATION DEVICE, AND COMPUTER SOFTWARE THEREOF

CROSS REFERENCE TO RELATED APPLICATIONS

This is a continuation application of International Application No. PCT/JP2012/00752 filed on Feb. 3, 2012, designating the United States of America, which is based on and claims priority of Japanese Patent Applications Nos. 2011-048369 filed on Mar. 4, 2011 and 2011-225375 filed on Oct. 12, 2011. The entire disclosures of the above-identified applications, including the specifications, drawings and claims are incorporated herein by reference in their entirety.

TECHNICAL FIELD

One or more exemplary embodiments disclosed herein relate generally to crystallinity evaluation methods, crystallinity evaluation devices, and their computer software, regarding crystalline semiconductor films.

BACKGROUND ART

For example, there are electronic devices such as a television receiver using an organic electro-luminescence (EL) display or a liquid crystal display. In such an electronic device, luminescence elements arranged in a matrix to form an organic display or a liquid crystal display are driven by a plurality of thin film transistors (TFT).

TFT is formed, for example, by sequentially stacking, on a substrate, a source electrode and a drain electrode, a semiconductor layer (channel layer), and a gate electrode. The channel layer used in the TFT is generally a thin-film silicon semiconductor (for example, Patent Literature 1).

Silicon semiconductor films are classified into amorphous silicon films (amorphous silicon: a-Si) and silicon films having crystallinity (crystalline silicon films). Crystalline silicon films can be further classified into polycrystalline silicon films, microcrystalline silicon films, monocrystalline silicon films, and the like.

Among them, amorphous silicon films can be manufactured homogeneously on a large-area substrate at a relatively low temperature by chemical vapor deposition (CVD) method or the like. Nowadays, amorphous silicon films are most commonly used as channel layers for liquid crystal elements of a large screen. However, amorphous silicon films have properties such as carrier mobility which is deteriorated in comparison to crystalline silicon films. Therefore, in order to achieve displays with higher-speed driving and higher definition, it is desired to implement TFTs made of crystalline silicon films.

Meanwhile, examples of methods of forming a crystalline silicon film are a method of directly forming a crystalline silicon film in film forming (for example, Patent Literature 2) and a method of applying heat or light energy to a formed amorphous silicon film to be crystallized (for example, Patent Literature 3).

However, the crystalline silicon films formed by these methods have totally different film quality. In addition, even if crystalline silicon films are manufactured by the same method, they may have different film quality depending on crystallization conditions.

In general, regarding a semiconductor device having a crystalline semiconductor film as an active layer, it is known that film quality (such as crystallinity and defect density) of the active layer significantly affects properties of the device.

In other words, in a transistor element having a crystalline silicon film as a channel layer, film quality of the crystalline silicon film significantly affects properties of the element, such as carrier mobility, a threshold voltage, and reliability.

For the above reasons, in order to use a crystalline semiconductor film as an active layer in a semiconductor device, it is necessary to evaluate and manage quality of the film. For the film quality management, it is desirable to manage, in particular, crystallinity.

As techniques of evaluating crystallinity of crystalline semiconductors, methods using Transmission Electron Microscope (TEM), X-ray Diffraction Technique (XRD), Photo Luminescence (PL), and the like are generally used. However, these techniques have difficulty in conducting in-line non-destructive evaluations of microscopic regions in a short period of time.

Therefore, there is Raman spectroscopy as a technique satisfying the above requirements (conducting the in-line non-destructive evaluations of microscopic regions in a short period of time).

The following describes the Raman spectroscopy with reference to the drawings.

FIG. 25 is a diagram schematically showing Raman scattering by incident light and molecular energy exchange.

Raman scattering is phenomenon caused by interaction between light and atoms oscillating in a material. More specifically, Raman scattering is phenomenon where, when light with oscillation frequency $v_0$ is incident onto a material in which nucleus is oscillating with oscillation frequency $v$, two waves having the different oscillation frequencies intervene with each other and light with oscillation frequency $v_{0+v}$ and light with oscillation frequency $v_{0-v}$ are incident together with the light with oscillation frequency $v_0$.

Here, as shown in (b) in FIG. 25, light scattering providing the same oscillation frequency as that of the incident light is called Rayleigh scattering, and light scattering providing oscillation frequency $v_{0\pm v}$ is called Raman scattering. Among the Raman scattering, components having oscillation frequency $v_{0-v}$ are called Stokes scattering ((a) in FIG. 25), and components having oscillation frequency $v_{0+v}$ are called Anti-Stokes scattering ((c) in FIG. 25) to be distinguished from each other.

Furthermore, an oscillation frequency difference $\pm v$ between incident light and Raman scattering light is called Raman shift. As this Raman shift is unique to a material, the Raman shift is a useful clue for material properties.

As explained above, the Raman spectroscopy is a technique of irradiating laser light to a specimen and measuring occurred Raman scattering light to easily perform non-destructive non-contact measurement and microscopic region evaluation. As a result, microscopic physicality can be examined.

For example, Patent Literature 4 discloses a method of manufacturing a semiconductor device by managing crystallinity of a crystalline silicon film by Raman spectroscopy. Patent Literature 4 discloses a method by which, when a-Si is laser-crystallized to be formed, the crystallization is performed observing a waveform or a full-width at half maximum (or FWHM) of a Raman peak as the crystallization state. In addition, for example, Patent Literature 5 discloses a method of managing crystallinity of a crystalline silicon film based on a Raman spectrum measured by Raman spectroscopy. It is disclosed in Patent Literature 5 that a crystalline silicon film is formed on a substrate, a peak waveform of a Raman band corresponding to a phonon unique to the crystalline silicon film is measured by Raman spectrometry, and crystallinity is managed based on a degree of asymmetry of this peak waveform.

CITATION LIST

Patent Literature

Patent Literature 1: Japanese Unexamined Patent Application Publication No. 6-342909
Patent Literature 2: Japanese Unexamined Patent Application Publication No. 61-153277
Patent Literature 3: Japanese Patent Publication No. 3535241
Patent Literature 4: Japanese Unexamined Patent Application Publication No. 3-109719
Patent Literature 5: Japanese Patent Publication No. 3305592

SUMMARY OF INVENTION

Technical Problem

However, the methods disclosed in the above-described Patent Literatures 4 and 5 fail to correctly evaluate (analyze) crystallinity of crystalline silicon films.

More specifically, the technique disclosed in the above-described Patent Literature 4, as information regarding crystallinity based on a Raman spectrum waveform of a crystalline silicon film, a peak intensity or its FWHM obtained by mathematically analyzing the waveform is used. However, these parameters are affected by measurement conditions, a sample state, and the like, and therefore do not always reflect only crystallinity. It is therefore impossible to correctly evaluate/analyze crystallinity by using there parameters.

Furthermore, the technique disclosed in the above-described Patent Literature 5, as information regarding crystallinity based on a Raman spectrum waveform of a crystalline silicon film, information obtained by mathematically analyzing peak asymmetry is used to manage crystallinity. However, this analysis method has poor physical grounds and therefore has a difficulty in correctly analyzing a Raman spectrum. In other words, it is impossible to correctly evaluate (analyze) crystallinity by using this analysis method.

Conventionally, an analysis method by which peaks at a plurality of phonon modes are assumed by a Gaussian function or the like has been widely used. However, this analysis method also has a problem of poor reproducibility of experimental results. In other words, it is impossible to correctly evaluate (analyze) crystallinity by using this analysis method. The following explains this analysis method in more detail, providing examples.

FIG. 26 is a graph plotting a Raman spectrum 500 of a crystalline silicon film and an analysis result 501 of the conventional analysis method. In FIG. 26, a vertical axis indicates a normalized Raman peak intensity, and a horizontal axis indicates a Raman shift (difference from incident light).

Here, it is assumed that the Raman spectrum 500 of the crystalline silicon film which is an experimental value includes, as shown in FIG. 26, three components which are: a crystalline silicon component 502 (peak position: 520 $cm^{-1}$), a microcrystalline silicon component 503 (peak position: up to 500 $cm^{-1}$), and an a-Si component 504 (peak position: up to 480 $cm^{-1}$), and that phonon scattering of each component conforms to a Gaussian function. Then, the analysis result 501 indicates a fitting result drawn by analyzing the Raman spectrum 500 under the above assumption.

From the analysis result 501, discrepancy from the experimental value is observed in a range approximately from 400 $cm^{-1}$ to 500 $cm^{-1}$ which is indicated by arrows A to C in FIG. 26. Furthermore, a peak corresponding to each phonon shows that the crystalline silicon component 502 is analyzed with a FWHM greater than a physically assumed FWHM (approximately 4 $cm^{-1}$, depending on a measurement system). In short, the reproducibility of the experimental result is not good. Therefore, in the above-described conventional method for mathematically reproducing experimental results has a difficulty in correctly analyzing a Raman spectrum to manage crystallinity.

As described above, the conventional methods have their problems of difficulty in correctly evaluating and analyzing crystallinity of a crystalline silicon film in a polycrystalline state or a non-monocrystalline state by Raman spectroscopy.

Technical Problem

Thus, the present disclosure overcomes the problems of the conventional techniques as described above. One non-limiting and exemplary embodiment provides a crystallinity evaluation method and a crystallinity evaluation device each capable of correctly evaluating crystallinity of a crystalline semiconductor film having high-mobility properties without mobility variation, and a computer software for them.

Solution to Problem

In one general aspect, the techniques disclosed here feature: a crystallinity evaluation method of evaluating crystallinity of a semiconductor film formed above a substrate, the crystallinity evaluation method including: obtaining a peak waveform of a Raman band in a Raman spectrum of the semiconductor film using Raman spectrometry, the Raman band corresponding to a phonon mode unique to the semiconductor film, the peak waveform being a waveform of a wavelength range having a peak of the Raman band; generating a first waveform by fitting the obtained peak waveform of the Raman band by using a Gauss function, the first waveform being a waveform fit by the Gauss function; extracting a peak value of the first waveform; generating a second waveform by fitting the obtained peak waveform of the Raman band by using a Lorenz function based on the extracted peak value, the second waveform being a waveform fit by the Lorenz function; obtaining at least one of a peak value, a full-width at half maximum, and a wavelength indicating the peak value regarding the generated second waveform; and evaluating crystallinity of the semiconductor film based on the at least one of the peak value, the full-width at half maximum, and the wavelength indicating the peak value.

Additional benefits and advantages of the disclosed embodiments will be apparent from the Specification and Drawings. The benefits and/or advantages may be individually obtained by the various embodiments and features of the Specification and Drawings, which need not all be provided in order to obtain one or more of such benefits and/or advantages.

Advantageous Effects of Invention

The present disclosure according to one or more exemplary embodiments or features disclosed herein provide a crystallinity evaluation method and a crystallinity evaluation device each capable of correctly evaluating crystallinity of a crystalline semiconductor film having high-mobility properties without mobility variation, and a computer software for them.

BRIEF DESCRIPTION OF DRAWINGS

These and other advantages and features will become apparent from the following description thereof taken in conjunction with the accompanying Drawings, by way of non-limiting examples of embodiments of the present disclosure. In the Drawings.

DESCRIPTION OF EMBODIMENT(S)

Figure 1:
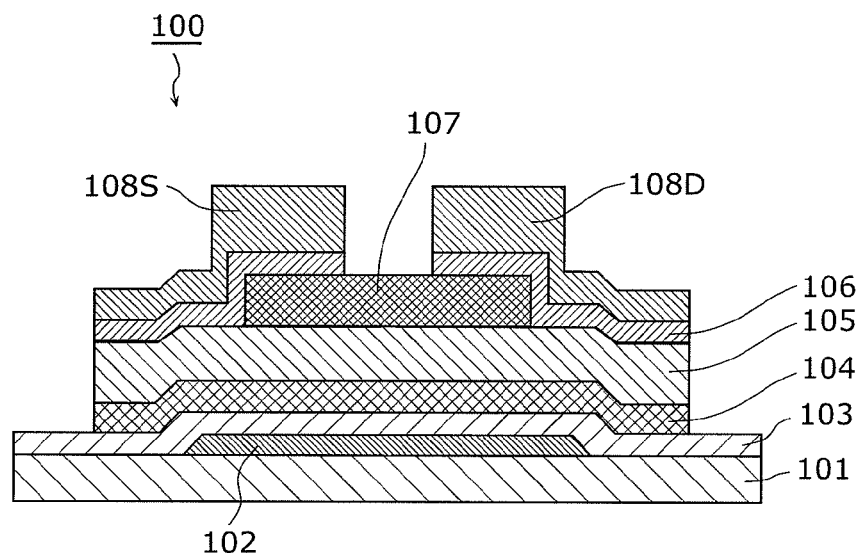
FIG. 1 is a cross-sectional schematically showing a structure of a TFT according to Embodiment 1.

According to an exemplary embodiment disclosed herein, there is a crystallinity evaluation method of evaluating crystallinity of a semiconductor film formed above a substrate, the crystallinity evaluation method including: obtaining a peak waveform of a Raman band in a Raman spectrum of the semiconductor film using Raman spectrometry, the Raman band corresponding to a phonon mode unique to the semiconductor film, the peak waveform being a waveform of a wavelength range having a peak of the Raman band; generating a first waveform by fitting the obtained peak waveform of the Raman band by using a Gauss function, the first waveform being a waveform fit by the Gauss function; extracting a peak value of the first waveform; generating a second waveform by fitting the obtained peak waveform of the Raman band by using a Lorenz function based on the extracted peak value, the second waveform being a waveform fit by the Lorenz function; obtaining at least one of a peak value, a full-width at half maximum (or FWHM), and a wavelength indicating the peak value regarding the generated second waveform; and evaluating crystallinity of the semiconductor film based on the at least one of the peak value, the full-width at half maximum, and the wavelength indicating the peak value.

In this way, it is possible to implement a crystallinity evaluation method and a crystallinity evaluation device each capable of correctly evaluating crystallinity of a crystalline semiconductor film having high-mobility properties without mobility variation, and a computer software for them.

For example, it is possible that the evaluating of the crystallinity of the semiconductor film by comparing (a) the at least one of the peak value, the full-width at half maximum, and the wavelength indicating the peak value to (b) at least one of a reference peak value, a reference full-width at half maximum, and a wavelength indicating the reference peak value which are previously stored in a lookup table, so as to evaluate the crystallinity of the semiconductor film, wherein in the lookup table, as the at least one of the reference peak value, the reference full-width at half maximum, and the wavelength indicating the reference peak value, at least one of a peak value, a full-width at half maximum, and a wavelength indicating the peak value regarding a third waveform is previously stored, the third waveform being generated prior to the obtaining of the peak waveform of the Raman band by fitting a peak waveform of a Raman band corresponding to a phonon mode unique to the crystalline semiconductor film by using the Lorenz function, and in the lookup table, a result of the evaluation of the crystallinity of the crystalline semiconductor film which includes a crystal grain size, an existence ratio of a crystal grain, and a mobility is stored in association with the at least one of the reference peak value, the reference full-width at half maximum, and the wavelength indicating the reference peak value.

According to another exemplary embodiment disclosed herein, there is a crystallinity evaluation method of evaluating crystallinity of a semiconductor film formed above a substrate, the crystallinity evaluation method including: obtaining a peak waveform of a Raman band in a Raman spectrum of the semiconductor film using Raman spectrometry, the Raman band corresponding to a phonon mode unique to the semiconductor film, the peak waveform being a waveform of a wavelength range having a peak of the Raman band; generating a waveform by fitting the obtained peak waveform of the Raman band by using a Raman spectrum function described by a Lorenz function based on the peak waveform, the waveform being a waveform fit by the Raman spectrum function; obtaining at least one of a peak value, a full-width at half maximum, and a wavelength indicating the peak value regarding the generated waveform; and evaluating crystallinity of the semiconductor film based on the at least one of the peak value, the full-width at half maximum, and the wavelength indicating the peak value, wherein the generating of the waveform includes: generating a Raman peak waveform analysis model expressed by Equation A, where $Ic(\omega)$ denotes a Raman band of a crystalline silicon component, $I\mu c(\omega)$ denotes a Raman band of a microcrystalline silicon component, $Ia(\omega)$ denotes a Raman band of an amorphous silicon component, $\sigma_c$ denotes a volume fraction of the crystalline silicon component, $\sigma_{mc}$ denotes a volume fraction of the microcrystalline silicon component, and $\sigma_a$ denotes a volume fraction of the amorphous silicon component; and describing each of the Raman band of the crystalline silicon component, the Raman band of the microcrystalline silicon component, and the Raman band of the amorphous silicon component, by using the Raman spectrum function as expressed by Equations B and C, where Lc denotes a phonon coherence length, $\alpha$ denotes a lattice constant, $\Gamma_0$ denotes a full-width at half maximum of a Raman peak of a monocrystalline semiconductor, and C denotes a normalized constant, $$I(\omega) = \sigma_a Ia(\omega) + \sigma_{mc} Iµc(\omega) + \sigma_c Ic(\omega) \quad \text{(Equation A)}$$

$$I(\omega) = C \int_0^{2\pi} d\varphi \int_{-\pi}^{\pi} \sin\theta \, d\theta \int_0^1 \left[ \frac{\exp\left(-\frac{q^2 Lc^2}{4a}\right)}{[\omega - \omega(q)]^2 + \left(\frac{\Gamma_0}{2}\right)^2} \right] q^2 \, dq \quad \text{(Equation B)}$$

where $$\sigma_a + \sigma_{mc} + \sigma_c = 1 \quad \text{(Equation C)}.$$

For example, it is possible that the evaluating of the crystallinity of the semiconductor film includes determining whether or not the full-width at half maximum is in a range from 5.0 cm$^{-1}$ to 6.0 cm$^{-1}$, so as to evaluate the crystallinity of the semiconductor film.

For example, it is possible that the semiconductor film is made of silicon, and the evaluating of the crystallinity of the semiconductor film includes determining whether or not a ratio of the full-width at half maximum to a full-width at half maximum of a Raman band of monocrystalline silicon is in a range from 1.5 to 1.8, so as to evaluate the crystallinity of the semiconductor film.

For example, it is possible that the semiconductor film is made of silicon, and the evaluating of the crystallinity of the semiconductor film includes determining whether or not a difference between the full-width at half maximum and a full-width at half maximum of a Raman band of the monocrystalline silicon is in a range from 1.8 cm$^{-1}$ to 2.4 cm$^{-1}$, so as to evaluate the crystallinity of the semiconductor film.

For example, it is possible that the evaluating of the crystallinity of the semiconductor film includes determining whether or not a ratio of the peak value to a full-width at half maximum of a Raman band of crystalline silicon is in a range from 0.1 to 0.2, so as to evaluate the crystallinity of the semiconductor film.

According to still another exemplary embodiment disclosed herein, there is a method of manufacturing a semiconductor film by evaluating crystallinity of a crystalline semiconductor film by using the crystallinity evaluation method according to Claim 1 so as to select the crystalline semiconductor film having predetermined crystallinity.

According to still another exemplary embodiment disclosed herein, there is a crystallinity evaluation device that evaluates crystallinity of a semiconductor film formed above a substrate, the crystallinity evaluation device including: a measurement unit configured to measure a Raman spectrum of the semiconductor film by Raman spectrometry so as to obtain a peak waveform of a Raman band corresponding to a phonon mode unique to the semiconductor film, the peak waveform being a waveform of a wavelength range having a peak of the Raman band; a first generation unit configured to generate a first waveform by fitting the obtained peak waveform of the Raman band by using a Gauss function, the first waveform being a waveform fit by the Gauss function; an extraction unit configured to extract a peak value of the first waveform; a second generation unit configured to generate a second waveform by fitting the obtained peak waveform of the Raman band by using a Lorenz function based on the extracted peak value, the second waveform being a waveform fit by the Lorenz function; an obtainment unit configured to obtain at least one of a peak value, a full-width at half maximum, and a wavelength indicating the peak value regarding the generated second waveform; and an evaluation unit configured to evaluate crystallinity of the semiconductor film based on the at least one of the peak value, the full-width at half maximum, and the wavelength indicating the peak value.

According to still another exemplary embodiment disclosed herein, there is a computer software recorded on a computer-readable recording medium, the computer software evaluating crystallinity of a crystalline semiconductor film, wherein the computer software includes a program causing a computer to execute the crystallinity evaluation method according to any one of Claims 1 to 7 to output a result of the evaluation of the crystallinity of the semiconductor film Hereinafter, certain exemplary embodiments are described in greater detail with reference to the accompanying Drawings.

Each of the exemplary embodiments described below shows a general or specific example. The numerical values, shapes, materials, structural elements, the arrangement and connection of the structural elements, steps, the processing order of the steps etc. shown in the following exemplary embodiments are mere examples, and therefore do not limit the inventive concept, the scope of which is defined in the appended Claims and their equivalents. Therefore, among the structural elements in the following exemplary embodiments, structural elements not recited in any one of the independent claims defining the most generic part of the inventive concept are described as arbitrary structural elements.

Embodiment 1

The following describes a TFT and a manufacturing method thereof according to the present disclosure based on embodiments, but the present disclosure is based on the claims. Therefore, although structural elements not described in the claims among the structural elements in the following embodiments are not always necessary to solve the problems, such structural elements are also described as being included in more desirable embodiments. It should also be noted that each of the figures is a schematic diagram and is not always depicted exactly.

First, the description is given for a structure of the TFT 100 according to the present embodiment. FIG. 1 is a cross-sectional view schematically showing a structure of a TFT according to Embodiment 1.

The TFT 100 shown in FIG. 1 is a channel-protection bottom-gate TFT. The TFT 100 includes: a substrate 101; a gate electrode 102 formed on the substrate 101; a gate insulating film 103 formed on the gate electrode 102; a crystalline silicon thin film 104 formed on the gate insulating film 103; an amorphous silicon thin film 105 formed on the crystalline silicon thin film 104; an insulation layer 107 formed on the amorphous silicon thin film 105; a source electrode 108S and a drain electrode 108D which are formed above the amorphous silicon thin film 105 so that the insulation layer 107 is located between (a) the amorphous silicon thin film 105 and (b) the source electrode 108S and the drain electrode 108D. Furthermore, the TFT 100 according to the present embodiment includes a pair of contact layers 106 each formed above the crystalline silicon thin film 104 and between the amorphous silicon thin film 105 and one of the source electrode 108S and the drain electrode 108D. The following describes each of the constituent elements of the TFT 100 according to the present embodiment.

The substrate 101 is a glass substrate made of glass such as silica glass, alkali-free glass, or high heat resistance glass. It should be noted that, in order to prevent that impurity such as natrium and phosphorus included in the glass substrate enters the crystalline silicon thin film 104, it is possible to form an undercoat layer made of, for example, a silicon nitride film ($SiN_x$), oxide silicon ($SiO_y$), or silicon oxide nitride film ($SiO_yN_x$), or the like on the substrate 101. The undercoat layer may serve to relax influence of heat on the substrate 101 in high-temperature heat treatment process such as laser annealing. A thickness of the undercoat layer is, for example, in a range approximately from 100 nm to 2000 nm.

The gate electrode 102 is patterned on the substrate 101 to have a predetermined shape. The gate electrode 102 may be a single-layer structure or a multi-layer structure of a conducting material, an alloy of the conduction materials, or the like. The gate electrode 102 is, for example, made of molybdenum (Mo), aluminum (Al), copper (Cu), tungsten (W), titanium (Ti), chromium (Cr), molybdenum tungsten (MoW), or the like. A thickness of the gate electrode 102 is, for example, in a range approximately from 20 nm to 500 nm. In the case of using high-temperature process such as laser annealing, it is desirable to use a material made of a high melting point metal such as molybdenum or tungsten for the gate electrode.

The gate insulating film 103 is formed on the gate electrode 102. The gate insulating film 103 is formed on the overall top surface of the substrate 101 to cover the gate electrode 102 in the present embodiment. The gate insulating film 103 is, for example, a single-layer film of oxide silicon ($SiO_y$), nitride silicon ($SiN_x$), silicon oxide nitride ($SiO_yN_x$), oxide aluminum ($AlO_z$), or oxide tantalum ($TaO_w$), or a multi-layer film including these films. A thickness of the gate insulating film 103 is, for example, in a range from 50 nm to 300 nm.

It should be noted in the present embodiment that since the crystalline silicon thin film 104 as the channel layer is included, the gate insulating film 103 at the interface with the channel layer is desirably made of oxide silicon. This is because the interface state between the crystalline silicon thin film 104 and the gate insulating film 103 is desirably good to maintain good threshold voltage properties of the TFT 100 and to achieve high mobility, and the oxide silicon is suitable for the desire.

The crystalline silicon thin film 104 corresponds to a semiconductor film of the present disclosure. The crystalline silicon thin film 104 is a first channel layer made of a semiconductor film formed on the gate insulating film, and has a predetermined channel region that is a region in which carrier mobility is controlled by a voltage of the gate electrode 102. The channel layer is a region above the gate electrode 102. A length of the channel region in a charge mobility direction corresponds to a gate length. The crystalline silicon thin film 104 may be, for example, formed by crystallizing amorphous silicon without crystallinity.

Here, an average crystal grain size of the crystalline silicon of the crystalline silicon thin film 104 is in a range approximately from 50 nm to 300 nm. A thickness of the crystalline silicon thin film 104 is, for example, in a range approximately from 20 nm to 100 nm. In addition, crystallinity of the crystalline silicon thin film 104 is expressed by the following way. A Raman band FWHM (hereinafter, referred to also as a "Raman FWHM") corresponding to a phonon mode unique to the crystalline silicon thin film 104 is in a range from 5.0 $cm^{-1}$ to 6.0 $cm^{-1}$. Here, the phonon mode unique to the crystalline silicon thin film 104 is a Transverse Optical (TO) phonon mode.

Moreover, crystallinity of the crystalline silicon thin film 104 may be expressed by the different way. For example, a ratio of a Raman FWHM of the crystalline silicon thin film 104 to a Raman FWHM of a monocrystalline silicon may be in a range from 1.5 to 1.8. Or, a difference between a Raman FWHM of the crystalline silicon thin film 104 and a Raman FWHM of a monocrystalline silicon substrate may be in a range from 1.8 $cm^{-1}$ to 2.4 $cm^{-1}$. Furthermore, a ratio (peak value/Raman FWHM) of a peak value of a Raman band of the crystalline silicon thin film 104 to a Raman FWHM of a polycrystalline silicon thin film may be in a range from 0.1 to 0.2. Here, the peak position of the Raman band of the crystalline silicon thin film 104 is in a range from 516 $cm^{-1}$ to 518 $cm^{-1}$, and a value of the Raman FWHM of the monocrystalline silicon (c-Si) is 3.4 $cm^{-1}$.

The field effect mobility of the crystalline silicon thin film 104 is in a range from 20 $cm^2/VS$ to 50 $cm^2/VS$, if the crystalline silicon thin film 104 has the above-described structure.

The amorphous silicon thin film 105 is a second channel layer formed on the crystalline silicon thin film 104 including the channel region. The amorphous silicon thin film 105 according to the present embodiment is an intrinsic amorphous silicon film. Here, a thickness of the amorphous silicon thin film 105 according to the present embodiment ranges, for example, from 10 nm to 40 nm. The amorphous silicon thin film 105 serves to relax electric field concentration at drain ends during transistor operation. In short, the amorphous silicon thin film 105 functions as an electric field relaxation layer.

The insulation layer 107 protects the channel layers (the crystalline silicon thin film 104 and the amorphous silicon thin film 105). The insulation layer 107 functions as a channel etching stopper (CES) layer to prevent the amorphous silicon thin film 105 from being etched in etching to form the pair of contact layers 106. The insulation layer 107 is formed above the crystalline silicon thin film 104 including the channel region and on the amorphous silicon thin film 105.

Furthermore, the insulation layer 107 is an organic material layer made of an organic material including mainly an organic material including silicon, oxygen, and carbon, or an inorganic material layer made of an inorganic material such as oxide silicon ($SiO_x$) or nitride silicon ($SiN_y$). Here, the insulation layer 107 has insulation properties, and the contact layers 106 in the pair are not electrically connected to each other.

Each of the contact layers 106 in the pair is made of an amorphous semiconductor film including high-density impurity, and formed above the crystalline silicon thin film 104 and the amorphous silicon thin film 105 via the insulation layer 107. Each of the contact layers 106 in the pair is, for example, an n-type semiconductor layer generated by doping phosphorus (P) as impurity into amorphous silicon, and more specifically, an $n^+$ layer including high-density impurity of $1 \times 10^{19}$ [$atm/cm^3$] or more. Here, when a P-type TFT is to be manufactured, the contact layers 106 may be formed as P-type contact layers in each of which impurity such as boron (B) is doped.

The contact layers 106 in the pair are provided to face each other with a predetermined interval on the insulation layer 107. Each of the contact layers 106 in the pair is formed cover the top surface of the insulation layer 107 and the amorphous silicon thin film 105. According to the present embodiment, one of the pair of contact layers 106 is formed to cover one end of the insulation layer 107 and the amorphous silicon thin film 105, so as to cover the top part and the side surface of the end of the insulation layer 107 and the top surface of a part of the amorphous silicon thin film 105 close to the side surface of the end of the insulation layer 107. On the other hand, the other of the contact layers 106 in the pair is formed to cover the other end of the insulation layer 107 and the amorphous silicon thin film 105, so as to cover the top part and the side surface of the other end of the insulation layer 107 and the top surface of a part of the amorphous silicon thin film 105 close to the side surface of the other end of the insulation layer 107. It should be noted that a thickness of each of the contact layers 106 may be, for example, in a range 5 nm to 10 nm.

The contact layers 106 in the pair according to the present embodiment are provided between (a) the amorphous silicon thin film 105 and (b) the source electrode 108S and the drain electrode 108D, but are not formed on the side surfaces of the amorphous silicon thin film 105 and the side surfaces of the crystalline silicon thin film 104. The pair of contact layers 106 are formed with the amorphous silicon thin film 105 and the crystalline silicon thin film 104 above the same plane.

Here, each of the contact layers 106 in the pair may include two layers which are (a) a low-density electric field relaxation layer ($n^-$ layer) as a lower layer and (b) a high-density contact layer ($n^+$ layer) as an upper layer. In the low-density electric field relaxation layer, phosphorus of approximately $1 \times 10^{17}$ [$atm/cm^3$] is doped. The above-described two layers can be formed continuously by a Chemical Vapor Deposition (CVD) device.

The source electrode 108S and the drain electrode 108D in a pair are provided to face each other in a predetermined distance above the crystalline silicon thin film 104 and the amorphous silicon thin film 105. The pair of the source electrode 108S and the drain electrode 108D is formed on the pair of contact layers 106 above the same plane.

The source electrode 108S is formed over one end of the insulation layer 107 and the amorphous silicon thin film 105 via one of the contact layers 106. On the other hand, the drain electrode 108D is formed over the other end of the insulation layer 107 and the amorphous silicon thin film 105 via the other of the contact layers 106.

According to the present embodiment, each of the source electrode 108S and the drain electrode 108D may be a single-layer structure a multi-layer structure made of a conducting material, an alloy of the conduction materials, or the like. For example, each of the source electrode 108S and the drain electrode 108D is made of aluminum (Al), molybdenum (Mo), tungsten (W), copper (Cu), titanium (Ti), chromium (Cr), or the like. According to the present embodiment, each of the source electrode 108S and the drain electrode 108D is formed to have a three-layer structure of MoW/Al/MoW. Here, a thickness of each of the source electrode 108S and the drain electrode 108D may be, for example, in a range approximately from 100 nm to 500 nm.

Thus, the TFT 100 has the above-described structure.

In the TFT 100, regarding the crystalline silicon thin film 104 formed as the channel layer, a FWHM of a Raman band corresponding to an unique phonon mode satisfies a range from $5.0 \text{ cm}^{-1}$ to $6.0 \text{ cm}^{-1}$ and an average crystal grain size satisfies the range from 50 nm to 300 nm approximately.

With the above, the TFT 100 can include, as a channel layer, a crystalline silicon thin film having high-mobility properties without mobility variation.

Here, in the manufacturing method described later, the TFT 100 is formed to have a selected crystalline silicon thin film 104 by using a crystallinity evaluation method, crystallinity evaluation device, or its computer software according to the present disclosure. The crystallinity evaluation method and the like will be described later, so that they are not explained here. In the manufacturing method described below, by using the crystallinity evaluation method according to the present disclosure, a crystalline silicon thin film 104 at least satisfying a range from $5.0 \text{ cm}^{-1}$ to $6.0 \text{ cm}^{-1}$ of a FWHM of a Raman band corresponding to an unique phonon mode is selected.

Figure 2A:
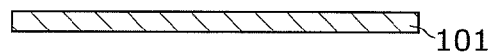
FIG. 2A is a cross-sectional view schematically showing a substrate preparation step in a method of manufacturing the TFT according to Embodiment 1.

The following describes a method of manufacturing the TFT 100 according to Embodiment 1 with reference to FIGS. 2A to SK. FIGS. 2A to SK are cross-sectional views schematically showing respective steps in the method of manufacturing the TFT according to Embodiment 1.

First, as shown in FIG. 2A, the substrate 101 is prepared. An example of the substrate 101 is a glass substrate. It should be noted that it is possible, prior to forming of the gate electrode 102, to form an undercoat layer made of a silicon nitride film, silicon oxide film, silicon oxide nitride film or the like on the substrate 101 by plasma CVD or the like.

Figure 2B:
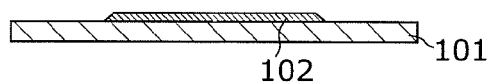
FIG. 2B is a cross-sectional view schematically showing a gate electrode forming step in the method of manufacturing the TFT according to Embodiment 1.

Next, as shown in FIG. 2B, the gate electrode 102 is patterned to have a predetermined shape above the substrate 101. For example, on the overall surface of the substrate 101, a gate metal film made of molybdenum tungsten (MoW) or the like is formed by spattering. Then, by applying a photolithography and wet etching, a gate metal film is patterned to form the gate electrode 102 having a predetermined shape. The Mow wet etching is performed using, for example, chemical that is a predetermined mixture of phosphoric acid ($HPO_4$), nitric acid ($HNO_3$), acetic acid ($CH_3COOH$), and water.

Figure 2C:
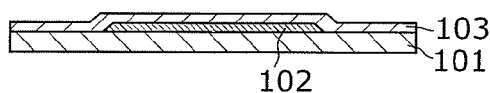
FIG. 2C is a cross-sectional view schematically showing a gate insulating film forming step in the method of manufacturing the TFT according to Embodiment 1.

Next, as shown in FIG. 2C, the gate insulating film 103 is formed above the substrate 101. For example, the gate insulating film 103 made of oxide silicon is formed overall above the substrate 101 so as to cover the gate electrode 102 by plasma CVD or the like. Here, it is possible to form the oxide silicon by, for example, introducing silence gas ($SiH_4$) and nitrogen monoxide ($N_2O$) at a predetermined concentration ratio.

Figure 2D:
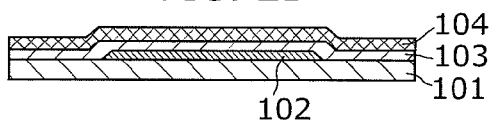
FIG. 2D is a cross-sectional view schematically showing a crystalline silicon layer forming step in the method of manufacturing the TFT according to Embodiment 1.

Next, as shown in FIG. 2D, the crystalline silicon thin film 104 made of crystalline silicon is formed on the gate insulating film 103. In more detail, first, on the gate insulating film 103, an amorphous silicon thin film made of, for example, amorphous silicon is formed by plasma CVD or the like. After dehydrogenative annealing treatment, laser annealing is performed on the amorphous silicon thin film to be crystallized to form the crystalline silicon thin film 104. Here, it is possible to form the amorphous silicon thin film by, for example, introducing silence gas ($SiH_4$) and hydrogen gas ($H_2$) at a predetermined concentration ratio. The dehydrogenative annealing treatment may be performed, for example, at 450° C. to 550° C. and for approximately 5 minutes to 1 hour.

It should be noted in the present embodiment that the amorphous silicon thin film is crystallized by laser annealing using green laser, but the crystallization method may be a laser annealing method using pulse laser having a wavelength in a range approximately from 370 nm to 900 nm, or a laser annealing method using continuous wave laser having a wavelength in a range approximately from 370 nm to 900 nm.

After that, hydrogen plasma treatment is performed on the crystalline silicon thin film 104 to hydrogenate silicon atoms in the crystalline silicon thin film 104. The hydrogenation is performed, for example, by producing hydrogen plasma by radio-frequency (RF) power from gas including hydrogen gas such as $H_2$ or $H_2$/Argon (Ar), and irradiating the hydrogen plasma on the crystalline silicon thin film 104. The hydrogenation causes hydrogen termination of dangling-bond defect of silicon atoms, and reduces crystallinity defect density of the crystalline silicon thin film 104 to improve crystallinity.

Here, according to the present embodiment, the crystallinity evaluation method or the like according to the present disclosure is used to select the crystalline silicon thin film 104 having desired properties. More specifically, first, by using the crystallinity evaluation method or the like according to the present disclosure, a value (peak intensity, FWHM, Raman shift amount, or the like) indicating crystallinity of the crystalline silicon thin film 104 is evaluated. Subsequently, based on the obtained value (peak intensity, FWHM, Raman shift amount, or the like) indicating crystallinity of the crystalline silicon thin film 104, a crystalline silicon thin film 104 having desired properties is selected. For example, as a value indicating desirable film quality conditions, namely, desirable crystallinity of the crystalline silicon thin film 104, it is examined whether or not a FWHM of a Raman band corresponding to a phonon mode unique to the crystalline silicon thin film satisfies a range from 5.0 cm$^{-1}$ to 6.0 cm$^{-1}$. Then, in the examination, only a crystalline silicon thin film 104 satisfying the above conditions is selected. By the above method, it is possible to select only crystalline silicon thin films 104 having high-mobility properties without mobility variation as desired properties, and provide the films to the subsequent processing step. It should be noted that an average crystal grain size of the above-described selected crystalline silicon thin film 104 is in a range approximately from 50 nm to 300 nm.

It should also be noted that a method of selecting only crystalline silicon thin films 104 having high-mobility properties without mobility variation is not limited to the above. For example, regarding a value indicating crystallinity of the crystalline silicon thin film 104, it is possible to select a crystalline silicon thin film 104 satisfying a ratio of a Raman FWHM of the crystalline silicon thin film 104 to a Raman FWHM of a monocrystalline silicon in a range from 1.5 to 1.8, or to select a crystalline silicon thin film 104 satisfying a different between a Raman FWHM of the crystalline silicon thin film 104 and a Raman FWHM of a monocrystalline silicon substrate in a range from 1.8 cm$^{-1}$ to 2.4 cm$^{-1}$. It is further possible to select a crystalline silicon thin film 104 satisfying a ratio (peak value/Raman FWHM) of a peak value of a Raman band of the crystalline silicon thin film 104 to a Raman FWHM of a polycrystalline silicon thin film in a range from 0.1 to 0.2. Here, the peak position of the Raman band of the crystalline silicon thin film 104 is in a range from 516 cm$^{-1}$ to 518 cm$^{-1}$, and a value of the Raman FWHM of the monocrystalline silicon (c-Si) is 3.4 cm$^{-1}$.

Figure 2E:
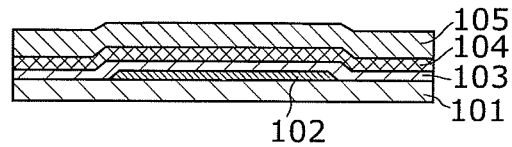
FIG. 2E is a cross-sectional view schematically showing a amorphous silicon layer forming step in the method of manufacturing the TFT according to Embodiment 1.

Next, as shown in FIG. 2E, the amorphous silicon thin film 105 is formed on the crystalline silicon thin film 104. In more detail, after forming the crystalline silicon thin film 104, the amorphous silicon thin film 105 that is an amorphous silicon film is formed under predetermined film-forming conditions (forming conditions) by plasma CVD or the like.

Figure 2F:
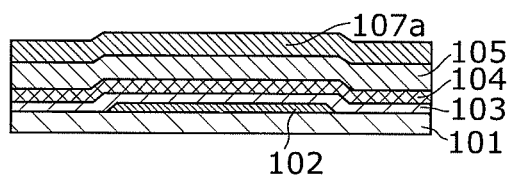
FIG. 2F is a cross-sectional view schematically showing an insulating layer forming film forming step in the method of manufacturing the TFT according to Embodiment 1.

Next, as shown in FIG. 2F, an insulation layer forming film 107a for forming the insulation layer 107 is formed on the amorphous silicon thin film 105. The insulation layer forming film 107a is made of an inorganic material.

For example, in the case where the insulation layer forming film 107a is made of an inorganic material such as oxide silicon, resist having a predetermined width (not shown) is formed on the insulation layer forming film 107a as a photo mask for defining the insulation layer 107 to have a predetermined shape.

Figure 2G:
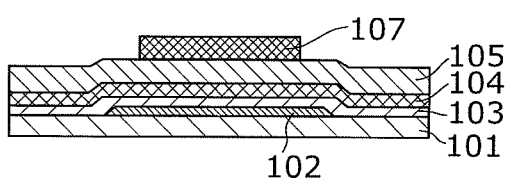
FIG. 2G is a cross-sectional view schematically showing a convex part forming step (etching step) in the method of manufacturing the TFT according to Embodiment 1.

Next, the resist is dry-etched as a mask, so as to pattern, as shown in FIG. 2G, the insulation layer forming film 107a to form the insulation layer 107 having the predetermined shape. Next, the resist formed on the insulation layer 107 is removed. Therefore, the top surface of the insulation layer 107 is exposed.

Figure 2H:
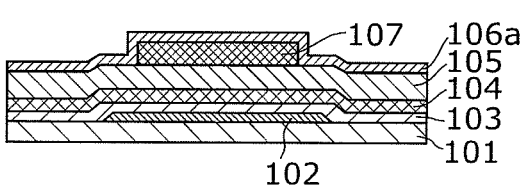
FIG. 2H is a cross-sectional view schematically showing a contact layer forming film forming step in the method of manufacturing the TFT according to Embodiment 1.

Next, as shown in FIG. 2H, a contact layer forming film 106a to be the contact layers 106 is formed on the amorphous silicon thin film 105 to cover the insulation layer 107. In more detail, the contact layer forming film 106a made of amorphous silicon doped with impurity of quinquevalent element such as phosphorus is formed by, for example, plasma CVD, so that the contact layer forming film 106a covers the top surface of the insulation layer 107 and the planer part of the amorphous silicon thin film 105.

It should be noted that the contact layer forming film 106a may include two layers of a low-density electric field relaxation layer and a high-density contact layer. The low-density electric field relaxation layer can be formed by doping phosphorus of approximately 1×10$^{17}$ [atm/cm$^3$]. The above-described two layers can be formed continuously by a CVD device.

Figure 2I:
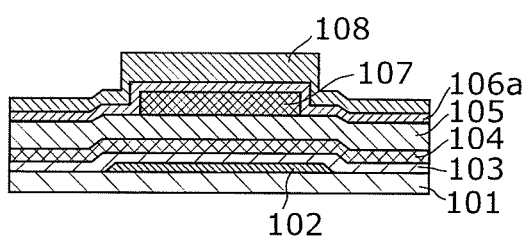
FIG. 2I is a cross-sectional view schematically showing a source-drain metal film forming step in the method of manufacturing the TFT according to Embodiment 1.
Figure 2J:
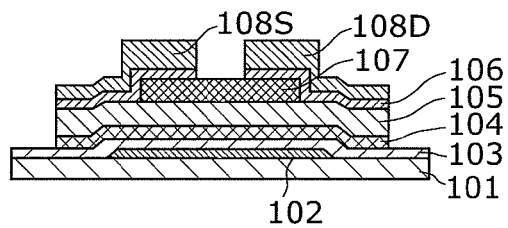
FIG. 2J is a cross-sectional view schematically showing a source electrode/drain electrode forming step in the method of manufacturing the TFT according to Embodiment 1.

Next, as shown in FIG. 2I, a source-drain metal film 108 to be the source electrode 108S and the drain electrode 108D is formed to cover the contact layer forming film 106a. For example, the source-drain metal film 108 having a three-layer structure of MoW/Al/MoW is formed by spattering.

After that, although not shown, in order to form the source electrode 108S and the drain electrode 108D having a predetermined shape, a resist material is applied on the source-drain metal film 108, and photolithography and development are performed on it to form a resist patterned in the predetermined shape.

Figure 23:
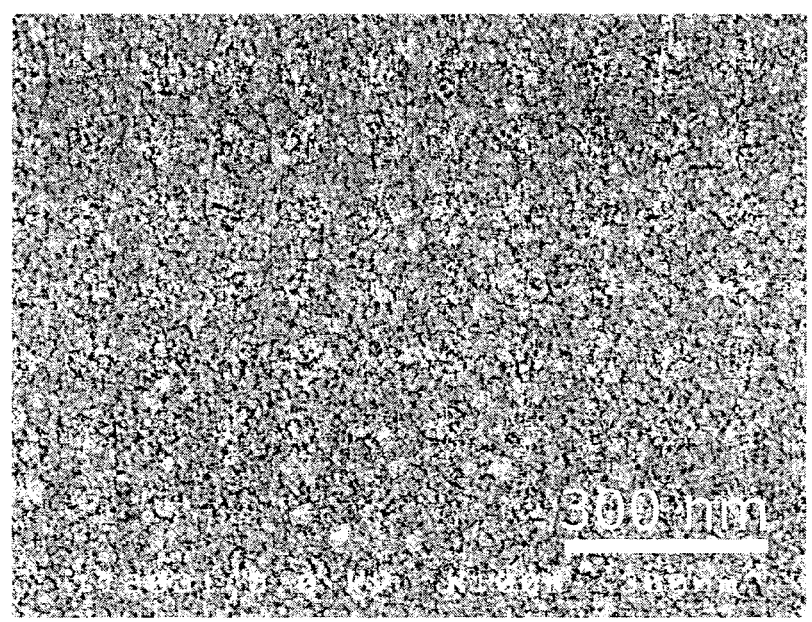
FIG. 23 is a diagram showing a planar electronic microscope image of a crystalline silicon film according to Example 2 of Embodiment 2.

Next, the resist is wet-etched as a mask to pattern the source-drain metal film 108, thereby forming, as shown in FIG. 23, the source electrode 108S and the drain electrode 108D having the predetermined shape. Here, the contact layer forming film 106a functions as an etching stopper. After that, the resist on the source electrode 108S and the drain electrode 108D is removed. Then, by dry-etching the source electrode 108S and the drain electrode 108D as masks, the contact layer forming film 106a is patterned to form the pair of contact layers 106 having the predetermined shape. Here, as conditions for the dry-etching, chlorinated gas may be used.

As described above, the TFT 100 according to the present embodiment can be manufactured.

Figure 2K:
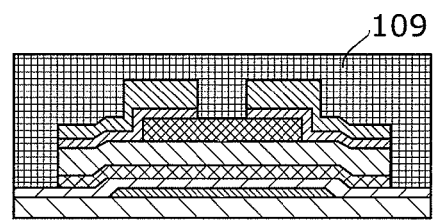
FIG. 2K is a cross-sectional view schematically showing a passivation film forming step in the method of manufacturing the TFT according to Embodiment 1.

After that, as shown in FIG. 2K, a passivation film 109 made of an inorganic material such as SiN may be formed over the entire the source electrode 108S and the drain electrode 108D.

It should be noted that the above description has been given, for the sake of simplicity in the description, for the method of manufacturing a single TFT, but the present disclosure is not limited to the above. It is also possible to manufacture a plurality of TFTs in an array, not only one TFT. In this case, in the step shown in FIG. 2D, it is possible to examine, as a representative, one of the crystalline silicon thin films 104 formed in an array. Then, after the examination, only crystalline silicon thin film(s) 104 satisfying the above conditions is/are selected. By this, it is possible to manufacture a plurality of TFTs made of crystalline silicon thin films having high-mobility properties without variation. As a result, these TFTs can be used in an organic EL panel or the like used for a large screen.

Next, the description is given for the method of selecting, in FIG. 2D, a crystalline silicon thin film 104 having desired properties by using the crystallinity evaluation method according to the present disclosure. More specifically, by using the crystallinity evaluation method, the crystallinity evaluation device, the their computer software, or the like according to the present disclosure, a value (peak intensity, FWHM, Raman shift amount, or the like) indicating crystallinity of the crystalline silicon thin film 104 is evaluated. Then, only a crystalline silicon thin film 104 having high-mobility propriety without mobility variation as the desired properties is selected.

Figure 3:
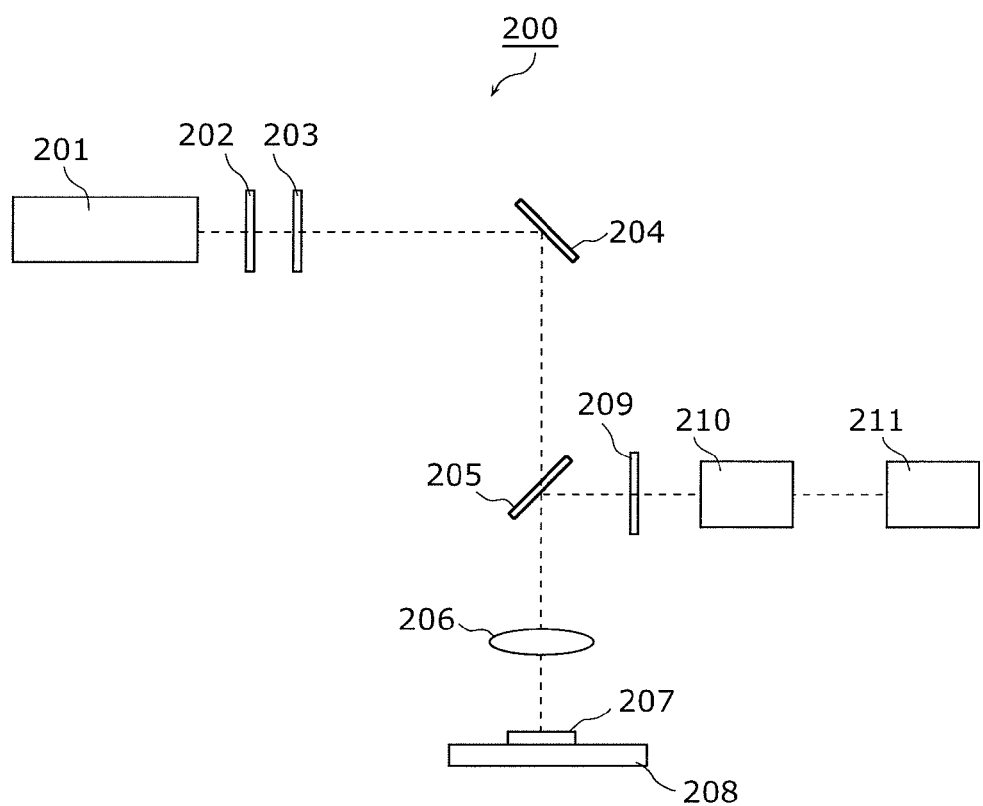
FIG. 3 is a schematic diagram of a Raman spectrometer used in crystallinity evaluation for a crystalline semiconductor film according to Embodiment 1.

FIG. 3 is a schematic diagram of a Raman spectrometer 200 used in crystallinity evaluation for a crystalline semiconductor film according to Embodiment 1. More specifically, evaluation (examination) of the crystalline silicon thin film 104, such as a Raman FWHM corresponding to a phonon mode unique to the crystalline silicon thin film 104, is performed by using the Raman spectrometer shown in FIG. 3, for example. The following describes the Raman spectrometer 200 shown in FIG. 3.

The Raman spectrometer 200 shown in FIG. 3 includes a light source 201, an attenuator 202, a filter 203, a mirror 204, a beam splitter 205, an objective lens 206, a stage 208, a slit 209, a spectrometer 210, and a detector 211. The Raman spectrometer 200 performs Raman spectrometry on a specimen 207. Here, the specimen 207 is a specimen in which a crystalline silicon thin film is formed on a gate electrode by the above-described manufacturing method, or is equivalent to such a specimen.

The light source 201 emits laser light having a wavelength in a range approximately from 470 nm to 700 nm. For example, the light source 201 emits argon ion later having a wavelength of 514.5 nm, YAG laser having a wavelength of 532 nm, or the like.

The attenuator 202 reduces the laser light emitted from the light source 201 not to affect the specimen 207.

The filter 203 extracts and passes light having a desired wavelength from the light reduced by the attenuator 202.

It should be noted that, in the present embodiment, laser power is adjusted not to change a spectrum of the specimen 207 depending on magnifying power of each objective lens in the light source 201 and the attenuator 202. For example, if each objective lens has 50 magnifications, laser power on the specimen 207 is adjusted to be in a range from 1 mW to 20 mW.

The mirror 204 controls a propagation direction of light having passed through the filter 203.

The beam splitter 205 leads the light propagated in the direction controlled by the mirror 204 to the objective lens 206 in a microscope system. The beam splitter 205 leads the scattering light, which has been scattered on a specimen surface of the specimen 207 and then collected by the objective lens 206, into the spectrometer 210 via the slit 209.

The objective lens 206 collects the light led via the beam splitter 205 so as to be incident on the specimen 207 on the stage 208. Here, by changing the magnifying power of the objective lens 206, it is possible to change the incident spot (spatial resolution) of the laser light on the surface of the specimen 207. For example, in the case of the objective lens 206 having 100 magnifications, an incident spot diameter of laser light on the specimen surface of the specimen 207 is set to approximately 0.6 μm.

In addition, the objective lens 206 collects the scattering light scattered on the specimen surface of the specimen 207 and leads the light into the beam splitter 205.

The slit 209 improves the spectrum resolution of the passing light by a width of the slit. Here, a narrower slit width increases the spectrum resolution, but decreases an intensity of the scattering light. Therefore, in view of resolution and S/N, the slit width should be appropriately set for each device. In the present embodiment, for example, the slit width is set to in a range approximately from 20 μm to 200 μm.

The spectrometer 210 is a device for resolving light depending on its wavelength so as to obtain a spectrum (scattered light). The spectrometer 210 scatters the light led via the slit 209. The spectrometer 210 is generally a single monochromator. If the number of gratings included in the spectrometer 210 is increased, the resolution is increased, but an obtained region of a spectrum is decreased and the intensity of the scattering light is reduced. Therefore, it is necessary to appropriately select the number of gratings (the number of grooves) for each target to be measured. According to the present embodiment, the number of grooves is, for example, in a range approximately from 1800 G/mm to 3000 G/mm.

The detector 211 detects the light scattered by the spectrometer 210 as signals, thereby obtaining a Raman spectrum. The detector 211 includes, for example, a photoelectron multiplication tube and a Charge Coupled Device (CCD). Here, a distance between the spectrometer 210 and the detector 211 is called a focal length. A longer focal length increases a frequency resolution of the spectrum but decreases the intensity of the scattering light. Therefore, according to the present embodiment, a focal length is set to in a range approximately from 250 nm to 500 mm.

Thus, the Raman spectrometer 200 has the above-described structure.

Next, a method of analyzing the Raman spectrum obtained by using the above-described Raman spectrometer 200 is described.

Figure 4:
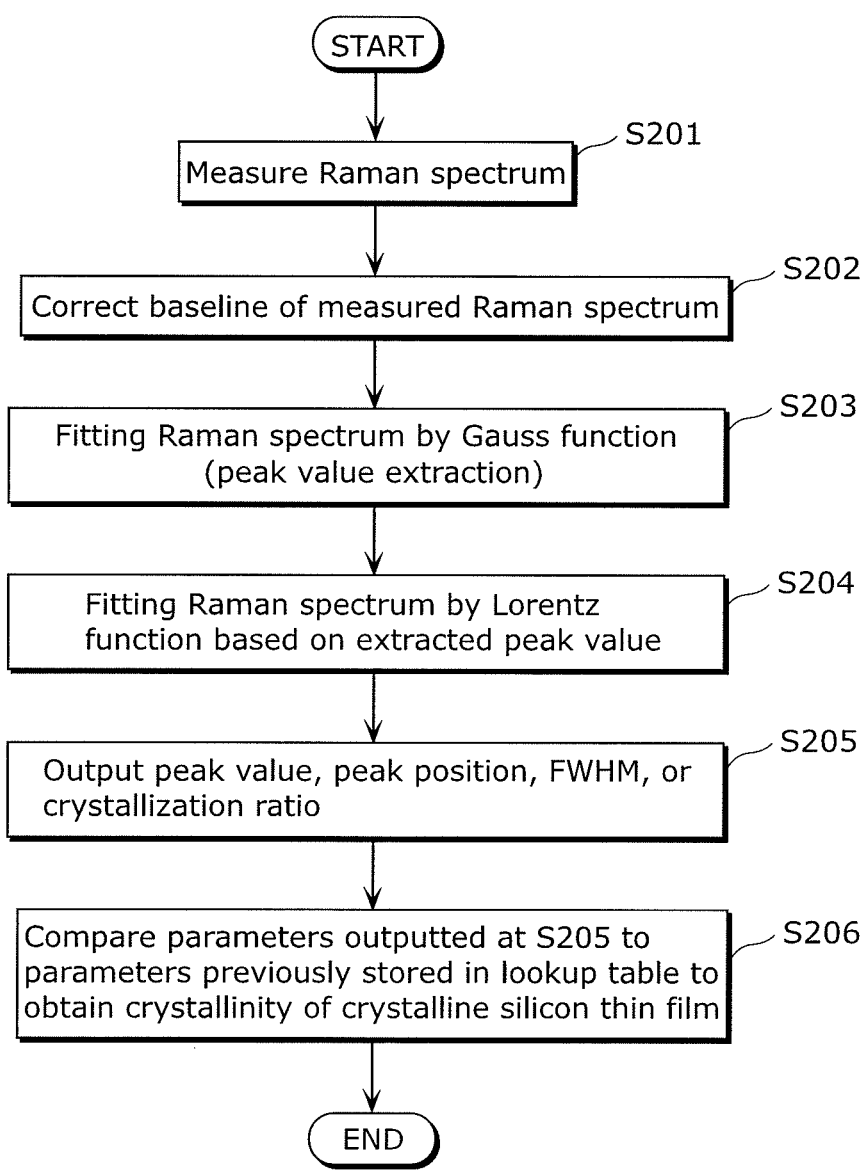
FIG. 4 is a flowchart for explaining a method of analyzing a Raman spectrum according to Embodiment 1.
Figure 5:
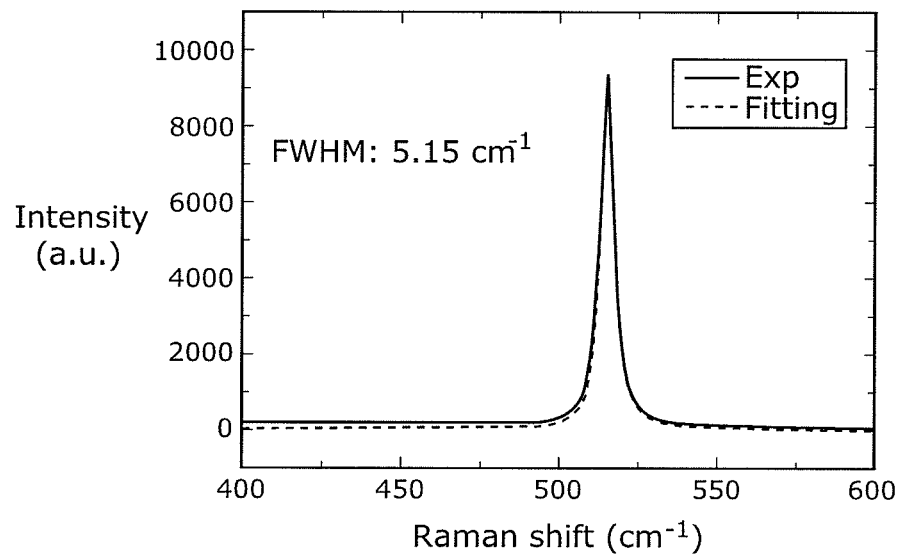
FIG. 5 is a graph plotting a Raman spectrum of a crystalline silicon thin film and its analysis result according to Embodiment 1.

FIG. 4 is a flowchart for explaining the method of analyzing a Raman spectrum according to Embodiment 1. FIG. 5 is a graph plotting the Raman spectrum of the crystalline silicon thin film and its analysis result according to Embodiment 1.

First, a Raman spectrum is measured by using the Raman spectrometer 200 (S201). More specifically, a peak waveform of a Raman band corresponding to a phonon mode unique to a semiconductor film is measured by Raman spectrometry. Further specifically, a peak waveform of a Raman band corresponding to a phonon mode unique to the crystalline silicon thin film is measured by Raman spectrometry. Here, Raman spectroscopy is a measuring method under the observation that a Raman shift is unique to a material. By Raman spectroscopy, laser light is incident on a specimen and the resulting Raman scattering light is measured. Therefore, it is possible to detect microscopic physicality by non-destructive non-contact measurement. For measuring conditions, it is assumed that a measuring position is the crystalline silicon thin film on the gate electrode, and that an excitation wavelength is 532 nm. It is further assumed that a measuring spot diameter is 1.3 μmΦ, and a frequency resolution is 1.5 cm$^{-1}$.

A peak of a Raman band corresponding to a phonon mode unique to the crystalline silicon thin film is observed in a range from 516 cm$^{-1}$ to 518 cm$^{-1}$. Furthermore, for the crystalline silicon film, a peak of a Raman band corresponding to a phonon mode unique to silicon is observed in a region ranging approximately from 450 cm$^{-1}$ to 550 cm$^{-1}$. A peak of a Raman band corresponding to a phonon mode unique to a monocrystalline silicon film is observed in a range approximately from 500 cm$^{-1}$ to 510 cm$^{-1}$. A peak of a Raman band corresponding to a phonon mode unique to an a-Si film is observed in a region of approximately 480 cm$^{-1}$. According to the present embodiment, in the measured spectrum (the Raman spectrum), the analysis is performed on a peak waveform of a Raman band corresponding to a phonon mode unique to the crystalline silicon thin film.

Next, a baseline of the measured Raman spectrum is corrected (S202). More specifically, after measuring the peak waveform of the Raman band corresponding to the phonon mode unique to the crystalline silicon thin film, a baseline of the measured peak waveform is corrected. For example, the baseline is corrected by using a method of performing straight-line approximation on the region for which the Raman spectrum has been analyzed. This is because the baseline of the Raman spectrum is inclined affected by the sample (here, the specimen 207) or the measurement environments. There is the case where the baseline is not inclined. In this case, it is not necessary to correct the baseline.

Next, fitting is performed on the measured Raman spectrum by using Gauss function (S203). More specifically, the peak waveform of the measured Raman band is fit by using Gauss function, so as to generate a first waveform that is fit by Gauss function. Then, a peak value of the first waveform is extracted. More specifically, a Raman peak waveform analysis model is generated by using Gauss function (Gauss distribution), and fitting (reproduction of the Raman spectrum) is performed on the generated Raman peak waveform analysis model in a height direction. Then, an intensity (peak value) of the fit Raman peak waveform analysis model (the first waveform) is extracted. According to the present embodiment, a Raman peak waveform analysis model of a Raman band of a crystalline silicon thin film is generated by using Gauss function (Gauss distribution). Then, in the Raman spectrum having the corrected baseline, fitting is performed on components of the crystalline silicon thin film, namely, a peak of a Raman band observed in a range from 516 cm$^{-1}$ to 518 cm$^{-1}$, so as to extract an intensity (peak value).

Next, by using the extracted peak value, fitting is performed on the Raman spectrum by Lorenz function (S204).

More specifically, the peak waveform of the Raman band is fit by Lorenz function by using the extracted peak value, so as to generate a second waveform that has been fit by Lorenz function. More specifically, a different Raman peak waveform analysis model is generated by using Lorenz function, and fitting is performed on the generated Raman peak waveform analysis model in a width direction of the Raman band of the crystalline silicon thin film.

In other words, according to the present embodiment, for the Raman band of the crystalline silicon thin film having the corrected baseline, first, fitting is performed on a peak value by using a Raman peak waveform analysis model generated by Gauss function. And then, another fitting is performed in a width direction by using another Raman peak waveform analysis model generated by Lorenz function. FIG. 5 shows the analysis results.

Next, based on the results of fitting the Raman spectrum at S204, parameters are extracted and outputted. More specifically, a peak value, a FWHM, or a wavelength indicating the peak value of the second waveform are outputted. More specifically, from the Raman peak waveform analysis model generated by the spectrum analysis, namely, the fitting at S204, a peak position, a FWHM (Raman FWHM), a peak value (peak intensity), a volume fraction (crystallization ratio), and the like of each component are extracted and outputted as parameters (S205).

Next, for example, parameters previously stored in a lookup table is compared to the parameters outputted at S205, so as to obtain a value indicating crystallinity of the crystalline silicon thin film (S206). More specifically, crystallinity of a target crystalline semiconductor film is evaluated based on the outputted peak value, FWHM, or wavelength (Raman shift amount) indicating the peak value.

In more detail, the peak value, the FWHM, or the wavelength (Raman shift amount) indicating the peak value, which are outputted at S205, are compared to a reference peak value, a reference FWHM, or a wavelength (Raman shift amount) indicating the reference peak value, which are previously stored in the lookup table, so as to evaluate crystallinity of the crystalline semiconductor film.

Here, the value indicating crystallinity of the crystalline silicon thin film is, for example, a FWHM (Raman FWHM) of a Raman band of the crystalline silicon thin film 104. Furthermore, the value indicating crystallinity of the crystalline silicon thin film may be a value of a ratio of a Raman FWHM of the crystalline silicon thin film 104 to a Raman FWHM of monocrystalline silicon, or a value of a difference between a FWHM of the crystalline silicon thin film 104 and a Raman FWHM of a monocrystalline silicon substrate.

Moreover, the value indicating crystallinity of the crystalline silicon thin film may be a value of a ratio (peak value/Raman FWHM) of a peak value of a Raman band of the crystalline silicon thin film 104 to a Raman FWHM of a monocrystalline silicon film.

Furthermore, as the reference peak value, the reference FWHM, or the wavelength indicating the reference peak value, the lookup table previously stores a peak value, a FWHM, or a wavelength indicating the peak value of a third waveform that has been generated prior to S201 by fitting a peak waveform of a Raman band corresponding to a phonon mode unique to the crystalline semiconductor film by using Lorenz function. Furthermore, in the lookup table, evaluation of the crystallinity of the crystalline semiconductor film which includes a crystal grain size, an existence ratio of crystal grain, and a mobility is stored in association with the reference peak value, the reference FWHM, or the wavelength indicating the reference peak value.

As described above, by analyzing the Raman spectrum obtained by the Raman spectrometer 200, a value indicating crystallinity of the crystalline silicon thin film is obtained.

It should be noted that the Raman spectrum obtained by using the Raman spectrometer 200 may be executed by an evaluation device that performs the above-described evaluation method. In this case, the evaluation device may include a measurement unit, a first generation unit, an extraction unit, a second generation unit, an output unit, and an evaluation unit. Here, the measurement unit measures a peak waveform of a Raman band corresponding to a phonon mode unique to the semiconductor film by Raman spectrometry. The first generation unit performs fitting on the peak waveform of the measured Raman band by using Gauss function, so as to generate the first waveform that is fit by Gauss function. The extraction unit extracts a peak value of the first waveform. The second generation unit performs fitting on the peak waveform of a Raman band by Lorenz function based on the extracted peak value, so as to generate the second waveform that is fit by Lorenz function. The evaluation unit evaluates crystallinity of the semiconductor film, based on the output unit outputting a peak value, a FWHM, or a wavelength indicating the peak value of the second waveform, and the outputted peak value, FWHM, or wavelength indicating the peak value.

It should be noted that the evaluation device may be implemented as a computer software causing a computer to execute the processing units in the evaluation device as steps. In other words, it is possible to evaluate crystallinity, by executing a computer having a computer software on which a program for performing the above-described crystallinity evaluation method is recorded.

Next, it is explained that crystallinity of a crystalline semiconductor film can be correctly evaluated by using the crystallinity evaluation method for evaluating crystallinity of crystalline semiconductor films according to the present disclosure.

Figure 6:
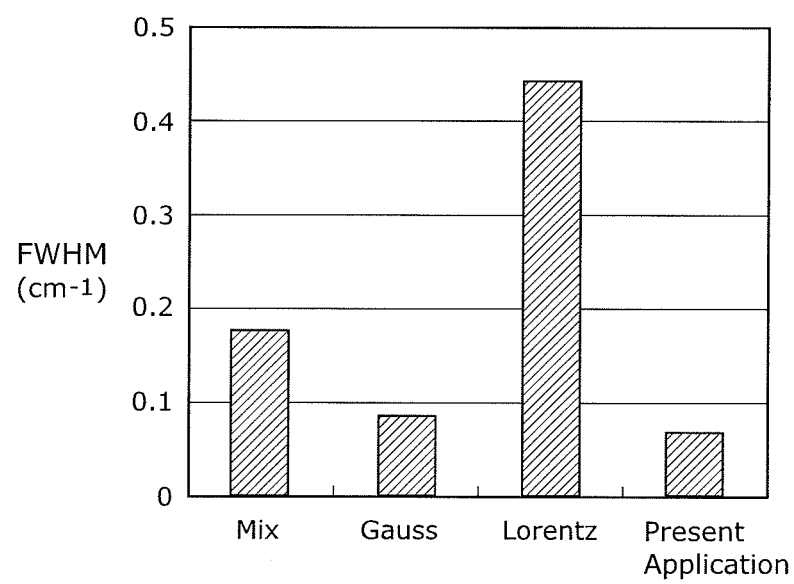
FIG. 6 is a graph plotting a relationship between a crystallinity evaluation method for a crystalline semiconductor film and variation of a value of FWHM.

FIG. 6 is a graph plotting a relationship between the crystallinity evaluation method of evaluating crystallinity of a crystalline semiconductor film and variation of a FWHM value. Here, a vertical axis indicates variation of a FWHM (cm$^{-1}$) of a Raman band, namely, a Raman FWHM variation, which is observed in a range from 516 cm$^{-1}$ to 518 cm$^{-1}$ when ten or more compositions crystallized at the same degree are measured. A horizontal axis indicates the method of evaluating the Raman FWHM of the measured Raman spectrum. More specifically, the present embodiment shown in FIG. 6 is an evaluation method for obtaining a Raman FWHM by fitting the measured Raman spectrum by Gauss function to obtain a peak value, and then performing fitting by Lorenz function using the peak value as an initial value. On the other hand, Gauss shown in FIG. 6 shows an evaluation method for obtaining a Raman FWHM by fitting the measured Raman spectrum only by Gauss function. Lorentz shown in FIG. 6 shows an evaluation method for obtaining a Raman FWHM by fitting the measured Raman spectrum only by Lorenz function. In addition, Mix in FIG. 6 shows an evaluation method for obtaining a Raman FWHM by fitting the measured Raman spectrum by a complex function (Voit function) in which Gauss function and Lorenz function are combined.

As shown in FIG. 6, in comparison to the conventional evaluation methods (Mix, Gauss, Lorentz), the evaluation method according to the present embodiment can reduce variations of the obtained Raman FWHMs. In other words, by using the evaluation method according to the present embodiment, it is possible to obtain a more correct Raman FWHM (a value indicating crystallinity of the crystalline silicon thin film).

Next, the description is given for a value indicating desired crystallinity (desirable film quality conditions) of the crystalline silicon thin film 104 of the TFT 100 according to the present embodiment.

Figure 7:
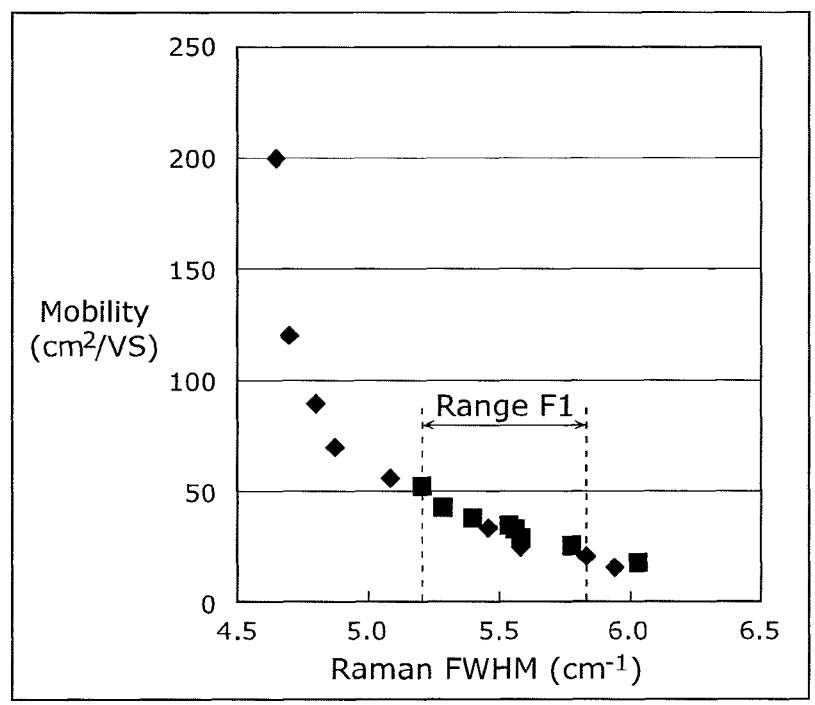
FIG. 7 is a graph plotting a relationship between (a) a mobility of a crystalline silicon thin film formed by the manufacturing method and (b) a Raman FWHM of the crystalline silicon thin film, according to Embodiment 1.
Figure 8:
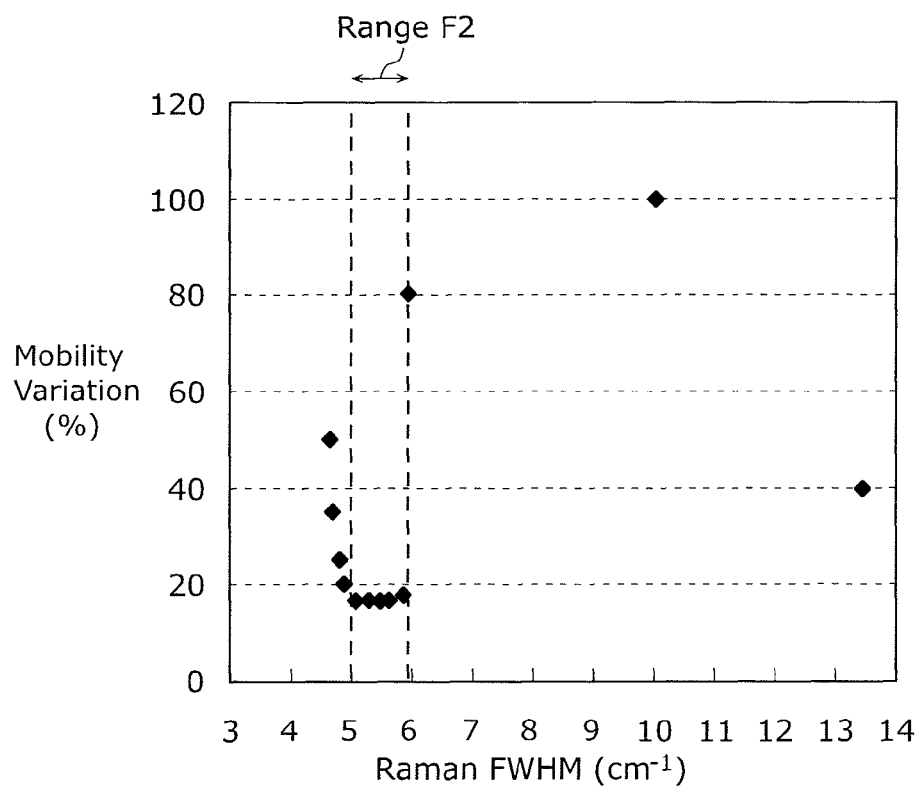
FIG. 8 is a graph plotting variation of an absolute value of the mobility in FIG. 7.

FIG. 7 is a graph plotting a relationship between (a) a mobility of the crystalline silicon thin film formed by the manufacturing method according to Embodiment 1 and (b) a Raman FWHM of the crystalline silicon thin film. Here, each data point in FIG. 7 corresponds to one of specimens 207 each of which is a crystalline silicon thin film formed on a gate electrode by the above-described manufacturing method. A vertical axis indicates a mobility ($cm^2/VS$). A horizontal axis indicates a FWHM ($cm^{-1}$) of a Raman band, namely, a Raman FWHM, which is observed in a range from 516 $cm^{-1}$ to 518 $cm^{-1}$. FIG. 8 is a graph plotting variation of an absolute value of the mobility in FIG. 7. More specifically, FIG. 8 is a graph showing a relationship between (a) variation of the absolute value of the mobility (FIG. 7) of the crystalline silicon thin film formed by the manufacturing method according to the present embodiment and (b) a Raman FWHM of the crystalline silicon thin film. Here, a vertical axis indicates variation (%) (3σ/average value×100) of a mobility of the crystalline silicon thin film. A horizontal axis indicates a Raman FWHM ($cm^{-1}$) of the crystalline silicon thin film.

It is seen in FIG. 8 that a range with less mobility variation is a range F2 in which a Raman FWHM ranges from 5.2 $cm^{-1}$ to 5.8 $cm^{-1}$.

It is thereby seen in FIG. 7 that a range with relatively less mobility variation is a range F1 in which mobility ranges from 20 $cm^2/VS$ to 50 $cm^2/VS$. This means that, in the range F1 where the Raman FWHM ranges from 5.2 $cm^{-1}$ to 5.8 $cm^{-1}$, a mobility ranges from 20 $cm^2/VS$ to 50 $cm^2/VS$.

Therefore, when the crystalline silicon thin film satisfies the Raman FWHM ranging from 5.0 $cm^{-1}$ to 6.0 $cm^{-1}$ as the desirable film quality conditions, the crystalline silicon thin film has desired property (the crystalline silicon thin film has high-mobility properties without mobility variation).

It is learned from the above that when the Raman FWHM of the crystalline silicon thin film satisfies the range from 5.2 $cm^{-1}$ to 5.8 $cm^{-1}$ as the desirable film quality conditions, the crystalline silicon thin film has desired property (high-mobility properties without mobility variation).

It is therefore possible to consider that when the Raman FWHM is smaller than 5 $cm^{-1}$, a grain size of the crystalline silicon thin film is large (large grain size) and mobility variation is increased. On the other hand, it is possible to consider that when the Raman FWHM is greater than 6 $cm^{-1}$, a grain size of the crystalline silicon thin film is small, but mobility variation is increased due to mixing of explosive crystal state (mix crystal of compositions melt partially with microcrystalline compositions).

As described above, at the manufacturing step for the TFT 100 shown in FIG. 2D, it is determined at S206 in FIG. 4 whether or not a Raman FWHM corresponding to a phonon mode unique to the crystalline silicon thin film satisfies the range from 5.0 $cm^{-1}$ to 6.0 $cm^{-1}$, thereby evaluating crystallinity of the crystalline semiconductor film. Then, in the TFT 100, the crystalline silicon thin film 104 satisfying the above-described conditions is selected to be a channel layer.

It should be noted that the a value indicating crystallinity of the crystalline silicon thin film having the desired properties (high-mobility properties without mobility variation) is a Raman FWHM of the crystalline silicon thin film, but the present embodiment is not limited to the above. The evaluation may be performed by using a ratio of a Raman FWHM of the crystalline silicon thin film to a Raman FWHM of monocrystalline silicon (c-Si), or a value of a difference between a Raman FWHM of the crystalline silicon thin film and a Raman FWHM of monocrystalline silicon. The following describes the examples with reference to FIGS. 9 and 10.

Figure 9:
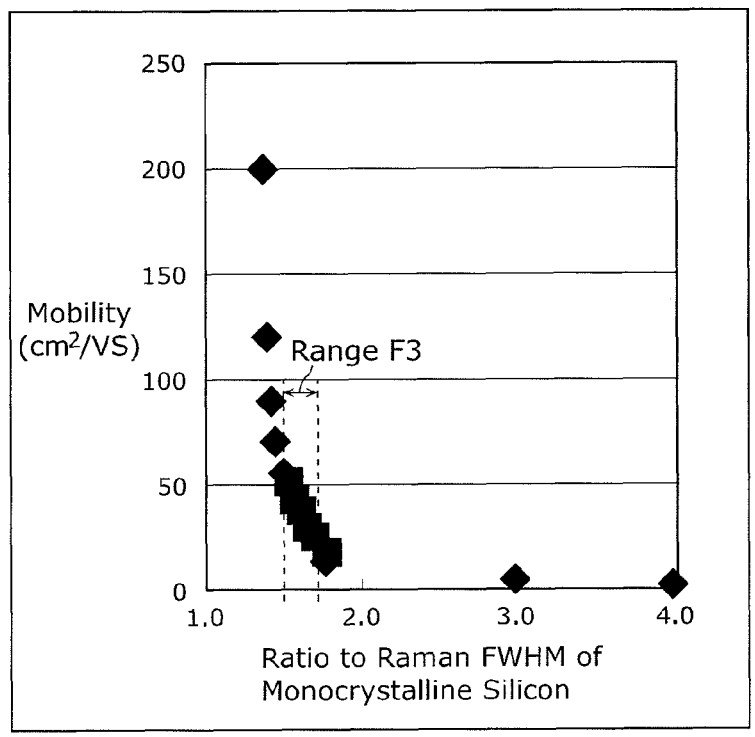
FIG. 9 is a graph plotting a relationship between (a) a mobility of a crystalline silicon thin film formed by the manufacturing method and (a) a ratio of a Raman FWHM of the crystalline silicon thin film to a Raman FWHM of a monocrystalline silicon, according to Embodiment 1.

FIG. 9 is a graph plotting a relationship between (a) a mobility of the crystalline silicon thin film formed by the manufacturing method according to the present embodiment and (a) a ratio of a Raman FWHM of the crystalline silicon thin film to a Raman FWHM of monocrystalline silicon (c-Si). Here, a vertical axis indicates mobility ($cm^2/VS$). A horizontal axis indicates a ratio of a Raman FWHM of the crystalline silicon thin film to a Raman FWHM of a monocrystalline silicon (c-Si). Furthermore, the Raman FWHM of the monocrystalline silicon (c-Si) is 3.4 $cm^{-1}$, and the Raman shift is a half-value of a Raman band of approximately 520 $cm^{-1}$.

In FIG. 9, a range F3 is a range in which a mobility ranges from 20 $cm^2/VS$ to 50 $cm^2/VS$. In the range F3, a ratio of a Raman FWHM of the crystalline silicon thin film to a Raman FWHM of a monocrystalline silicon (c-Si) is in a range from 1.5 to 1.8.

Therefore, at S206, it is determined whether or not the ratio of the Raman FWHM of the crystalline silicon thin film to the Raman FWHM of the monocrystalline silicon (c-Si) satisfies the range from 1.5 to 1.8, thereby evaluating whether or not the crystallinity of the crystalline semiconductor film has the desired properties. Then, when the above-described desirable film quality conditions are satisfied, the crystalline silicon thin film is evaluated as having the desired properties (high-mobility properties without mobility variation).

Figure 10:
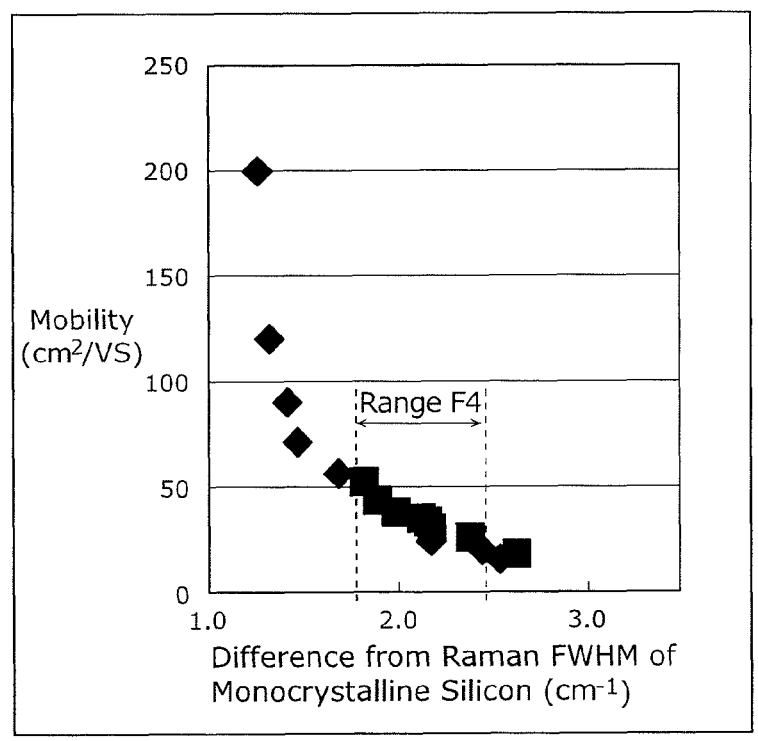
FIG. 10 is a graph plotting a relationship between (a) a mobility of a crystalline silicon thin film formed by the manufacturing method and (a) a difference between a Raman FWHM of the crystalline silicon thin film and a Raman FWHM of a monocrystalline silicon, according to Embodiment 1.

FIG. 10 is a graph plotting a relationship between (a) a mobility of the crystalline silicon thin film formed by the manufacturing method according to the present embodiment and (a) a difference between a Raman FWHM of the crystalline silicon thin film and a Raman FWHM of monocrystalline silicon (c-Si). Here, a vertical axis indicates a mobility ($cm^2/VS$). A horizontal axis indicates a value ($cm^{-1}$) obtained by subtracting the Raman FWHM of the monocrystalline silicon (c-Si) from the Raman FWHM of the crystalline silicon thin film. Here, a value of the Raman FWHM of the monocrystalline silicon is 3.4 $cm^{-1}$ (c-Si).

In FIG. 10, a range 4 is a range in which a mobility ranges from 20 $cm^2/VS$ to 50 $cm^2/VS$. In the range F4, the difference between the Raman FWHM of the crystalline silicon thin film and the Raman FWHM of the monocrystalline silicon (c-Si) ranges from 1.8 $cm^{-1}$ to 2.4 $cm^{-1}$.

Therefore, at S206, it is determined whether or not the difference between the Raman FWHM of the crystalline silicon thin film and the Raman FWHM of the monocrystalline silicon (c-Si) satisfies the range from 1.8 $cm^{-1}$ to 2.4 $cm^{-1}$, thereby evaluating whether or not the crystallinity of the crystalline semiconductor film has the desired properties. Then, when the above-described desirable film quality conditions are satisfied, the crystalline silicon thin film is evaluated as having the desired properties (high-mobility properties without mobility variation).

It should be noted that the a value indicating crystallinity of the crystalline silicon thin film having the desired properties (high-mobility properties without mobility variation) is a value calculated by using the Raman FWHM of the crystalline silicon thin film, but the present embodiment is not limited to the above. The following describes an example where a peak position or a peak value (peak intensity) of the Raman band of the crystalline silicon thin film is used.

Figure 11:
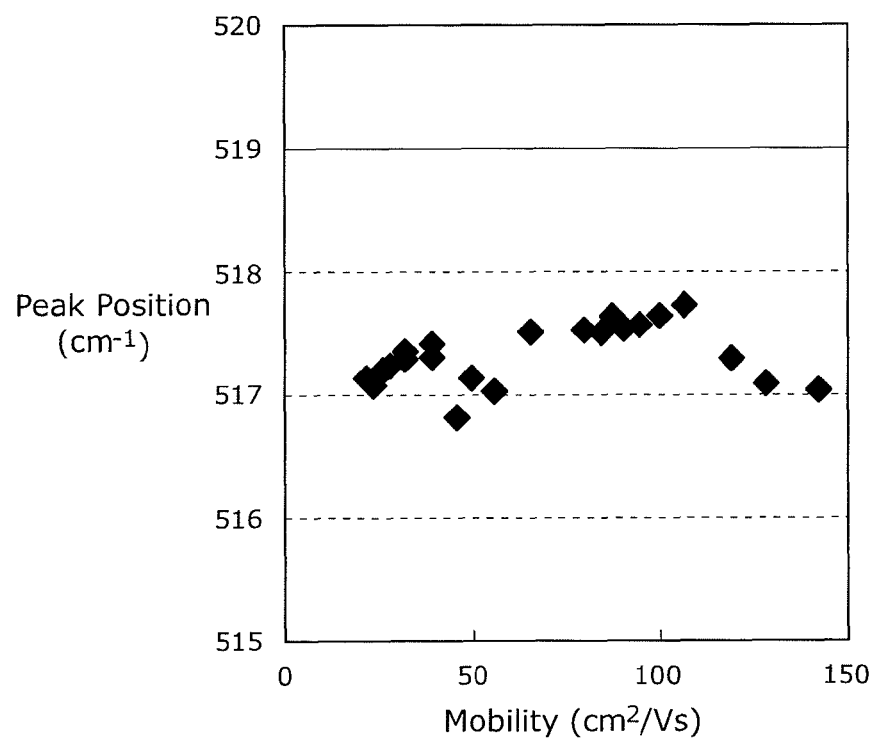
FIG. 11 is a graph plotting a relationship between (a) a mobility of a crystalline silicon thin film formed by the manufacturing method and (b) a peak position of the crystalline silicon thin film, according to Embodiment 1.

First, with reference to FIG. 11, a mobility of the crystalline silicon thin film for which a peak of a Raman band is observed in a range from 516 $cm^{-1}$ to 518 $cm^{-1}$.

FIG. 11 is a graph plotting a relationship between (a) a mobility of the crystalline silicon thin film formed by the manufacturing method according to the present embodiment and (b) a peak position of the crystalline silicon thin film. Here, a vertical axis indicates a peak position ($cm^{-1}$). A horizontal axis indicates a mobility ($cm^2$/VS) of the crystalline silicon thin film.

It is seen in FIG. 11 that the crystalline silicon thin film in which a peak of a Raman band is observed in a rage from 516 $cm^{-1}$ to 518 $cm^-$, the crystalline silicon thin film has a high mobility up to 150 $cm^2$/VS.

Next, the description is given for the desirable film quality conditions of the crystalline silicon thin film 104 based on a peak position or a peak value (peak intensity) of a Raman band of the crystalline silicon thin film.

Figure 12:
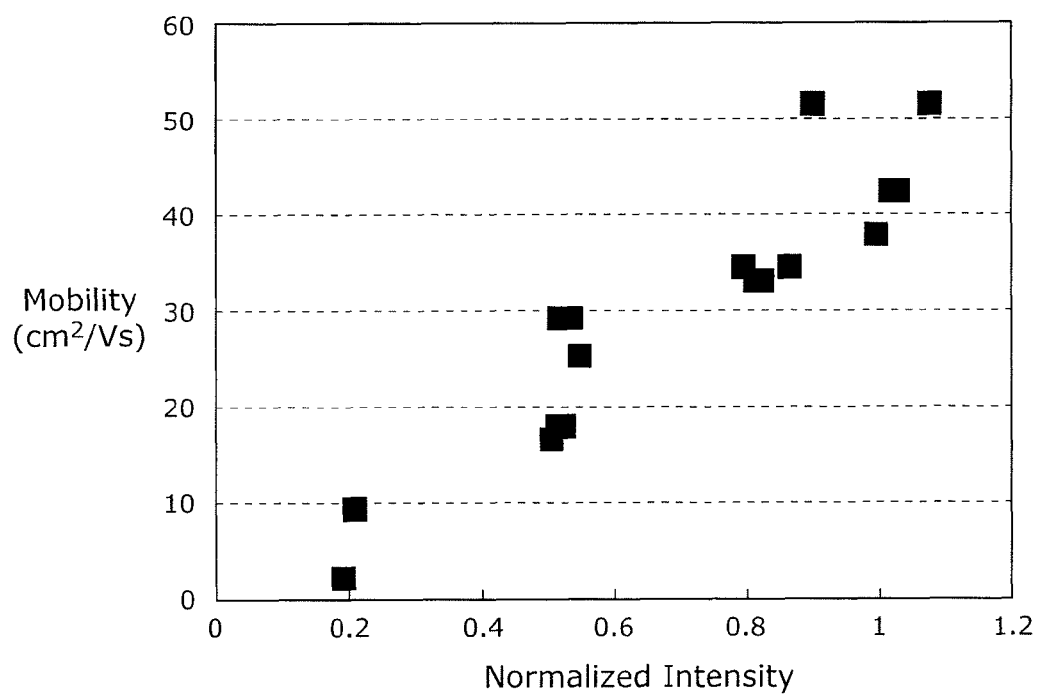
FIG. 12 is a graph plotting a relationship between (a) a mobility of a crystalline silicon thin film formed by the manufacturing method and (b) a normalized peak intensity of the crystalline silicon thin film, according to Embodiment 1.

FIG. 12 is a graph plotting a relationship between (a) a mobility of the crystalline silicon thin film formed by the manufacturing method according to the present embodiment and (b) a normalized peak intensity of the crystalline silicon thin film. Here, a vertical axis indicates a mobility ($cm^2$/VS). A horizontal axis indicates a peak intensity normalized by a peak intensity of the crystalline silicon thin film at a mobility of 40 $cm^2$/VS.

As shown in FIG. 12, in a mobility range from 20 $cm^2$/VS to 50 $cm^2$/VS, the normalized peak intensity of the crystalline silicon thin film ranges from 0.5 to 1.2.

Therefore, at S206, it is determined whether or not the normalized peak intensity of the crystalline silicon thin film satisfies the range from 0.5 to 1.2, thereby evaluating whether or not the crystallinity of the crystalline semiconductor film has the desired properties. Then, when the above-described desirable film quality conditions are satisfied, the crystalline silicon thin film is evaluated as having the desired properties (the crystalline silicon thin film has high-mobility properties without mobility variation).

Figure 13:
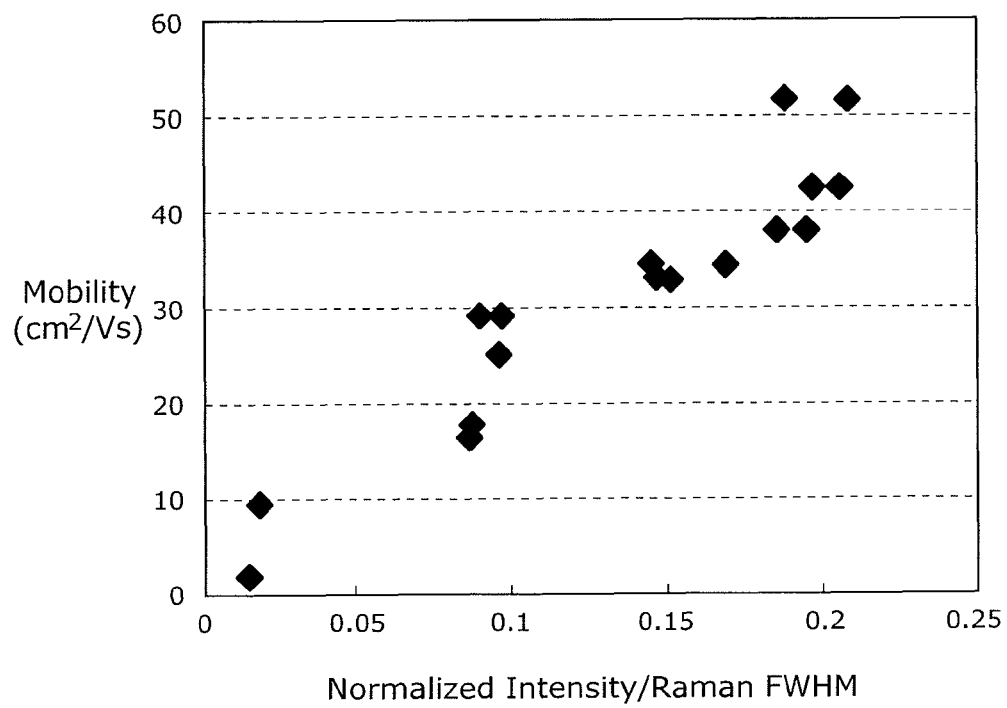
FIG. 13 is a graph plotting a relationship between (a) a mobility of a crystalline silicon thin film formed by the manufacturing method and (b) a ratio of a normalized peak intensity of the crystalline silicon thin film to a Raman FWHM, according to Embodiment 1.

FIG. 13 is a graph plotting a relationship between (a) a mobility of the crystalline silicon thin film formed by the manufacturing method according to the present embodiment and (b) a ratio of a normalized peak intensity of the crystalline silicon thin film to a Raman FWHM. Here, a vertical axis indicates a mobility ($cm^2$/VS) of the crystalline silicon thin film. A horizontal axis indicates a Raman FWHM normalized by a peak intensity of the crystalline silicon thin film at a mobility of 40 $cm^2$/VS.

As shown in FIG. 13, in a mobility range from 20 $cm^2$/VS to 50 $cm^2$/VS, the normalized Raman FWHM of the crystalline silicon thin film ranges from 0.1 to 0.2.

Therefore, at S206, it is determined whether or not the ratio of the normalized peak intensity of the crystalline silicon thin film to the Raman FWHM satisfies the range from 0.1 to 0.2, thereby evaluating whether or not the crystallinity of the crystalline semiconductor film has the desired properties. Then, when the above-described desirable film quality conditions are satisfied, the crystalline silicon thin film is evaluated as having the desired properties (high-mobility properties without mobility variation).

As described above, according to the present embodiment, the crystalline silicon thin film 104 having the desired properties are selected by using the crystallinity evaluation method or the like according to the present embodiment, and the selected crystalline silicon thin film 104 is used as a channel layer in the TFT. Thereby, it is possible to manufacture the TFT using, as the channel layer, the crystalline silicon thin film 104 having the desired properties (high-mobility properties without mobility variation).

It should be noted that it has been described that in the TFT according to the present embodiment, the channel protection layer is formed on the amorphous silicon thin film, but the present embodiment is not limited to the above. It is also possible that the channel protection layer is formed on the crystalline silicon thin film, and the amorphous silicon thin film is formed on the channel protection layer. The following describes them as variations.

(Variations)

Figure 14:
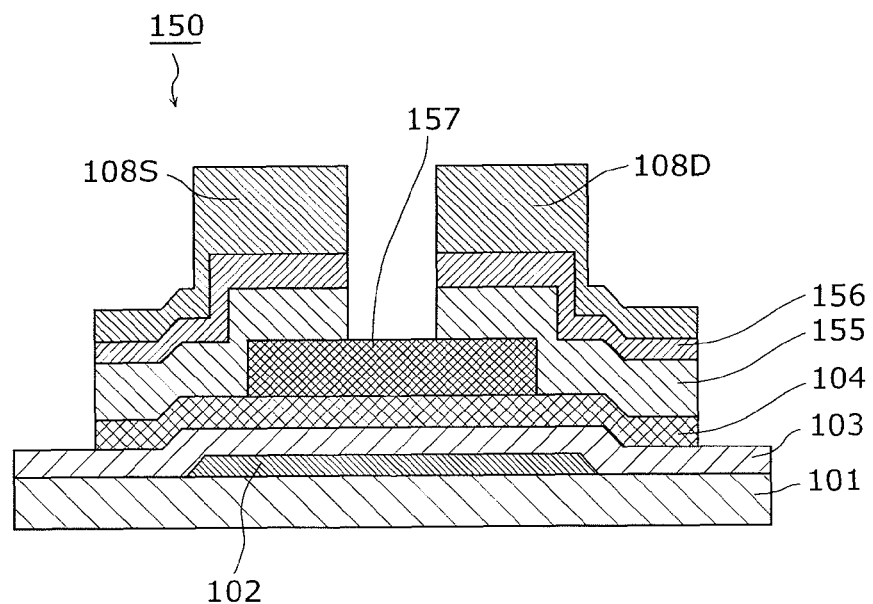
FIG. 14 is a cross-sectional view schematically showing a structure of a TFT according to a variation of Embodiment 1.

FIG. 14 is a cross-sectional view schematically showing a structure of a TFT according to a variation of Embodiment 1. Here, the same reference numerals of FIG. 1 are assigned to the identical elements of FIG. 14, so that the identical elements are not explained again below.

The TFT 150 shown in FIG. 14 differs from the TFT 100 according to the present embodiment in the structures of amorphous silicon thin films 155 and an insulation layer 157.

The insulation layer 157 protects the channel layer (the crystalline silicon thin film 104). The insulation layer 157 functions as a channel etching stopper (CES) to prevent the amorphous silicon thin films 155 from being etched in etching to form a pair of the amorphous silicon thin films 155 and a pair of the contact layers 156. The insulation layer 157 is formed on the amorphous silicon thin film 104 including the channel region. The material and the like of the insulation layer 157 is the same as those of the insulation layer 107, so that they are not described again.

The amorphous silicon thin films 155 in the pair are formed on the insulation layer 157 and the crystalline silicon thin film 104 including the channel region. The amorphous silicon thin films 155 in the pair are provided to face each other with a predetermined interval on the insulation layer 157. Each of the amorphous silicon thin films 155 in the pair is formed to cover a part of the top surface of the insulation layer 157 and a part of the crystalline silicon thin film 104. According to the variation of Embodiment 1, one of the pair of amorphous silicon thin films 155 is formed to cover one end of the insulation layer 157 and the crystalline silicon thin film 104, so as to cover the top part and the side surface of the end of the insulation layer 157 and the top surface of a part of the crystalline silicon thin film 104 close to the side surface of the end of the insulation layer 157. On the other hand, the other of the amorphous silicon thin films 155 in the pair is formed to cover the other end of the insulation layer 157 and the crystalline silicon thin film 104, so as to cover the top part and the side surface of the other end of the insulation layer 157 and the top surface of a part of the crystalline silicon thin film 104 close to the side surface of the other end of the insulation layer 157. The material and the like of the amorphous silicon thin films 155 in the pair is the same as those of the amorphous silicon thin film 105, so that they are not described again.

The contact layers 156 in the pair are provided to face each other with a predetermined interval above the insulation layer 157. Each of the contact layers 106 in the pair is formed on a corresponding one of the amorphous silicon thin films 155. The material and the like of the contact layers 156 in the pair is the same as those of the contact layers 106, so that they are not described again.

Thus, the TFT 150 has the above-described structure.

Next, a method of manufacturing the TFT 150 having the above-described structure is described. FIGS. 15A to 15K are cross-sectional views schematically showing respective steps in the method of manufacturing the TFT according to the variation of Embodiment 1.

FIGS. 15A to 15D show identical steps of FIGS. 2A to 2D, so that these steps are not described again.

Figure 15A:
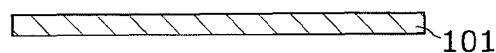
FIG. 15A is a cross-sectional view schematically showing a substrate preparation step in the method of manufacturing the TFT according to the variation of Embodiment 1.
Figure 15B:
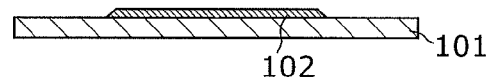
FIG. 15B is a cross-sectional view schematically showing a gate electrode forming step in the method of manufacturing the TFT according to the variation of Embodiment 1.
Figure 15C:
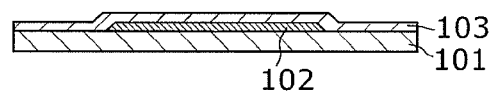
FIG. 15C is a cross-sectional view schematically showing a gate insulating film forming step in the method of manufacturing the TFT according to the variation of Embodiment 1.
Figure 15D:
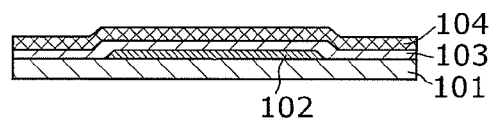
FIG. 15D is a cross-sectional view schematically showing a crystalline silicon layer forming step in the method of manufacturing the TFT according to the variation of Embodiment 1.
Figure 15E:
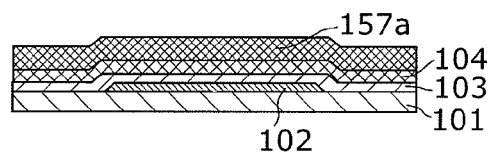
FIG. 15E is a cross-sectional view schematically showing an insulation layer forming film forming step in the method of manufacturing the TFT according to the variation of Embodiment 1.

Next, as shown in FIG. 15E, an insulation layer forming film 157a for forming the insulation layer 157 is formed on the crystalline silicon thin film 104. The insulation layer forming film 157a is made of an inorganic material. Here, for example, the insulation layer forming film 157a is made of an inorganic material such as oxide silicon or the like.

Figure 15F:
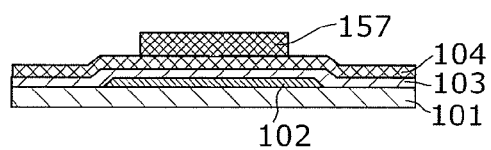
FIG. 15F is a cross-sectional view schematically showing an insulation layer forming step in the method of manufacturing the TFT according to the variation of Embodiment 1.

Next, a resist having a predetermined width is formed on the insulation layer forming film 157a as a photo mask for defining the insulation layer 157 to have a predetermined shape. After that, the resist is dry-etched as a mask, so as to pattern the insulation layer forming film 157a to form the insulation layer 157 having the predetermined shape. Next, the resist formed on the insulation layer 157 is removed. Thereby, as shown in FIG. 15F, the top surface of the insulation layer 157 is exposed.

Figure 15G:
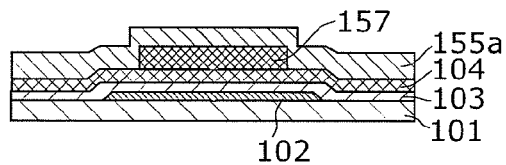
FIG. 15G is a cross-sectional view schematically showing an amorphous silicon layer forming step in the method of manufacturing the TFT according to the variation of Embodiment 1.

Next, as shown in FIG. 15G, the amorphous silicon thin films 155 are formed on the insulation layer 157 and the crystalline silicon thin film 104. In more detail, after forming the insulation layer 157, the amorphous silicon thin films 155 that are amorphous silicon films are formed under predetermined film-forming conditions (forming conditions) by plasma CVD or the like.

Figure 15H:
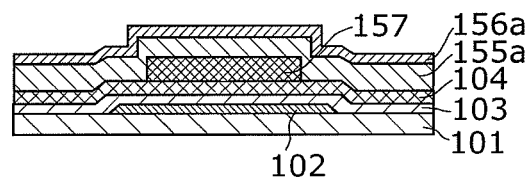
FIG. 15H is a cross-sectional view schematically showing a contact layer forming film forming step in the method of manufacturing the TFT according to the variation of Embodiment 1.

Next, as shown in FIG. 15H, a contact layer forming film 156a to be the contact layers 156 is formed on the amorphous silicon thin films 155. In more detail, the contact layer forming film 156a made of amorphous silicon doped with impurity of quinquevalent element such as phosphorus is formed on the amorphous silicon thin films 155 by, for example, plasma CVD.

It should be noted that the contact layer forming film 156a may include two layers of a low-density electric field relaxation layer and a high-density contact layer. The low-density electric field relaxation layer can be formed by doping phosphorus of approximately $1 \times 10^{17}$ [atm/cm$^3$]. The above-described two layers can be formed continuously by a CVD device.

Figure 15I:
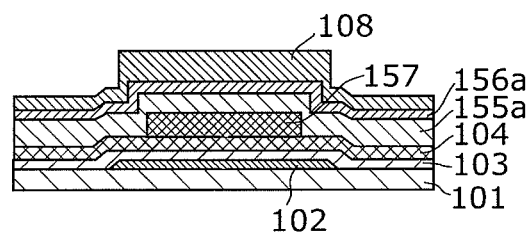
FIG. 15I is a cross-sectional view schematically showing a source-drain metal film forming step in the method of manufacturing the TFT according to the variation of Embodiment 1.

Next, as shown in FIG. 15I, a source-drain metal film 108 to be the source electrode 108S and the drain electrode 108D is formed to cover the contact layer forming film 156a. For example, the source-drain metal film 108 having a three-layer structure of MoW/Al/MoW is formed by spattering.

After that, although not shown, in order to form the source electrode 108S and the drain electrode 108D having a predetermined shape, a resist material is applied on the source-drain metal film 108, and photolithography and development are performed on it to form a resist patterned in the predetermined shape.

Figure 15J:
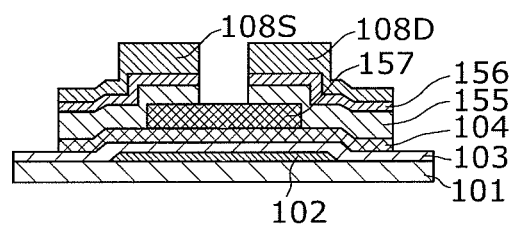
FIG. 15J is a cross-sectional view schematically showing a source electrode/drain electrode forming step in the method of manufacturing the TFT according to the variation of Embodiment 1.

Next, as shown in FIG. 15J, the resist is wet-etched as a mask to pattern the source-drain metal film 108, thereby forming the source electrode 108S and the drain electrode 108D having the predetermined shape. Here, the contact layer forming film 106a functions as an etching stopper. After that, the resist on the source electrode 108S and the drain electrode 108D is removed. Then, by dry-etching the source electrode 108S and the drain electrode 108D as masks, the contact layer forming film 156a and the amorphous silicon thin films 155 are patterned to form the pair of contact layers 156 and the pair of amorphous silicon thin films 155 having the predetermined shape. Here, as conditions for the dry-etching, chlorinated gas may be used.

As described above, the TFT 150 according to the variation of Embodiment 1 can be manufactured.

Figure 15K:
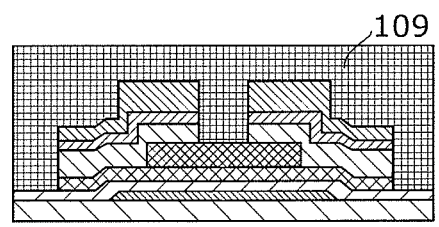
FIG. 15K is a cross-sectional view schematically showing a passivation film forming step in the method of manufacturing the TFT according to the variation of Embodiment 1.

After that, as shown in FIG. 15K, a passivation film 109 made of an inorganic material such as SiN may be formed over the entire the source electrode 108S and the drain electrode 108D.

As described above, the crystalline silicon thin film 104 having the desired properties is selected by using the crystallinity evaluation method or the like according to the present embodiment, and the selected crystalline silicon thin film 104 is used as a channel layer in the TFT. Thereby, it is possible to manufacture the TFT using, as the channel layer, the crystalline silicon thin film 104 having the desired properties (high-mobility properties without mobility variation).

In this way, according to the variation of Embodiment 1, it is possible to implement a crystallinity evaluation method, a crystallinity evaluation device, and computer software thereof each capable of correctly evaluating crystallinity of a crystalline semiconductor film having high-mobility characteristics without mobility variation, and a computer software for them.

It should be noted that the TFT according to the present embodiment can be applied not only to an organic EL display using organic EL elements, but also to other display devices, such as a liquid crystal display, which use an active matrix substrate. It should also be noted that the display devices having the above-described structure can be used as flat panel displays, and therefore can be applied to electronic devices, such as a television set, a personal computer, and a mobile telephone, which have various display panels.

Thus, although the crystallinity evaluation method, the crystallinity evaluation device, and the computer software thereof according to the present disclosure have been described based on the embodiment and the variation, the crystallinity evaluation method, the crystallinity evaluation device, and the computer software thereof according to the present disclosure are not limited to the above-described embodiment and variation.

For example, although it has been described in the above-described embodiment the evaluation of a crystalline semiconductor film included in a channel-protection TFT using an insulation layer (channel protection film), the present disclosure can be applied also to evaluation of a crystalline semiconductor film included in a channel-etching TFT without an insulation layer (channel protection film).

Furthermore, although it has been described regarding the crystallinity evaluation method, the crystallinity evaluation device, and the computer software thereof according to the present embodiment that an extracted peak value is used to perform fitting on a Raman spectrum by Lorenz function (S204), the present disclosure is not limited to the above. The fitting on a Raman spectrum may be performed by a function described by Lorenz function (for example, a Raman spectrum function described later) not by Lorenz function itself. In this case, it is possible to obtain a waveform having more reproducibility of a Raman spectrum.

Embodiment 2

The following describes a crystallinity evaluation method of evaluating crystallinity of a semiconductor film (hereinafter, referred to as a "film quality analysis method") according to Embodiment 2 in detail with reference to the drawings.

According to the present embodiment, Raman spectrometry for a crystalline silicon film is performed on a specimen 307 (not shown) by using the Raman spectrometer shown in FIG. 3.

Here, the specimen 307 is a crystalline silicon film formed by forming a base coat layer and amorphous silicon film (a-Si film) on a glass substrate and then crystallizing the amorphous silicon film to form the crystalline silicon film. The base coat film is, for example, a film having a low thermal conductivity, such as a silicon oxide film or a silicon nitride film having a thickness ranging approximately from 100 nm to 1 µm. The amorphous silicon film (a-Si film) is formed, for example, by depositing a film having a thickness ranging approximately from 20 nm to 200 nm by plasma CVD. A method of crystallizing the amorphous silicon film is laser or heat. Here, in the case of crystallization using laser (laser crystallizing method), a light source of pulse oscillation and continuous oscillation having a wavelength ranging from 200 nm to 1000 nm is used for crystallization. Prior to the crystallization using laser, dehydrogenative annealing ay be performed at 400° C. to 600° C. to prevent bumping of the amorphous silicon film (a-Si film).

Next, a method of analyzing the Raman spectrum obtained by using the Raman spectrometer 200 is described.

Figure 16:
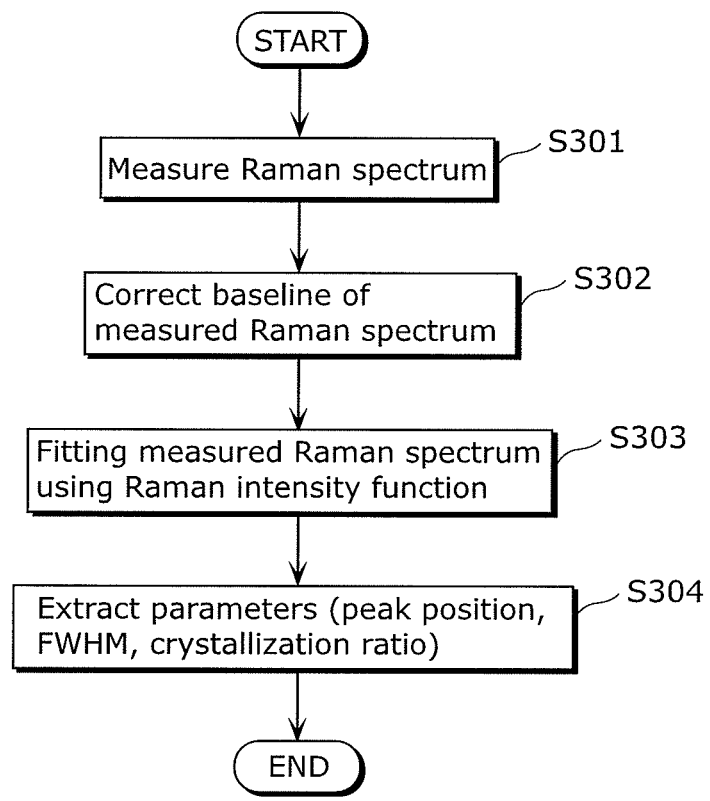
FIG. 16 is a flowchart for explaining an analysis method of a Raman spectrum used in film analysis for a crystalline semiconductor film according to Embodiment 2.
Figure 17A:
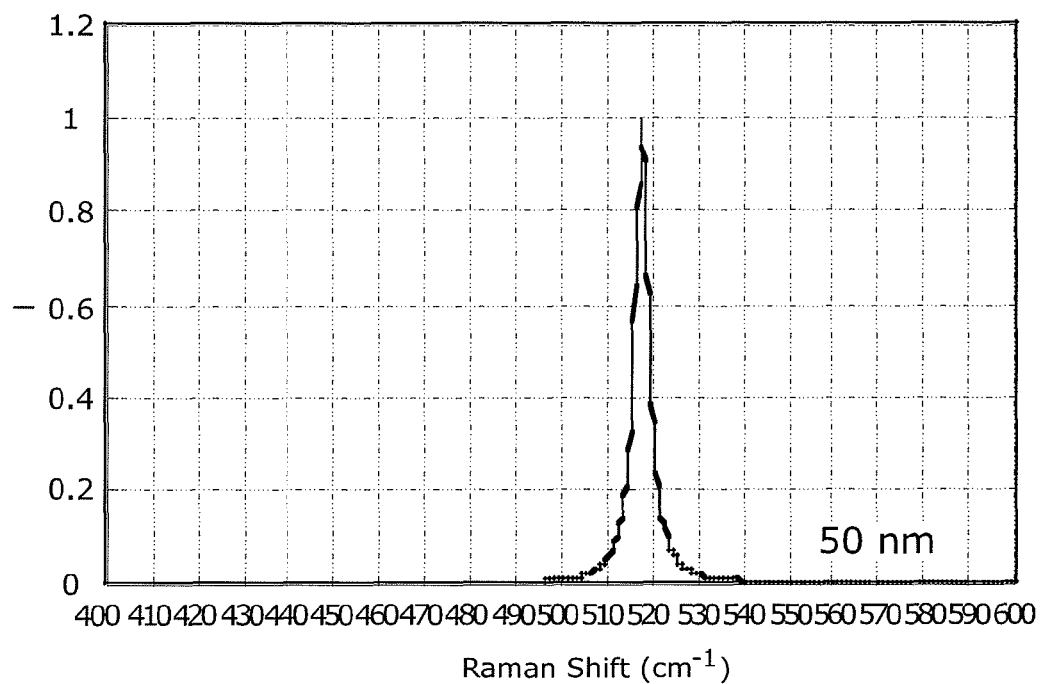
FIG. 17A is a graph plotting a result of calculating a Raman spectrum dependency of a coherence length of a phonon according to Embodiment 2.
Figure 17B:
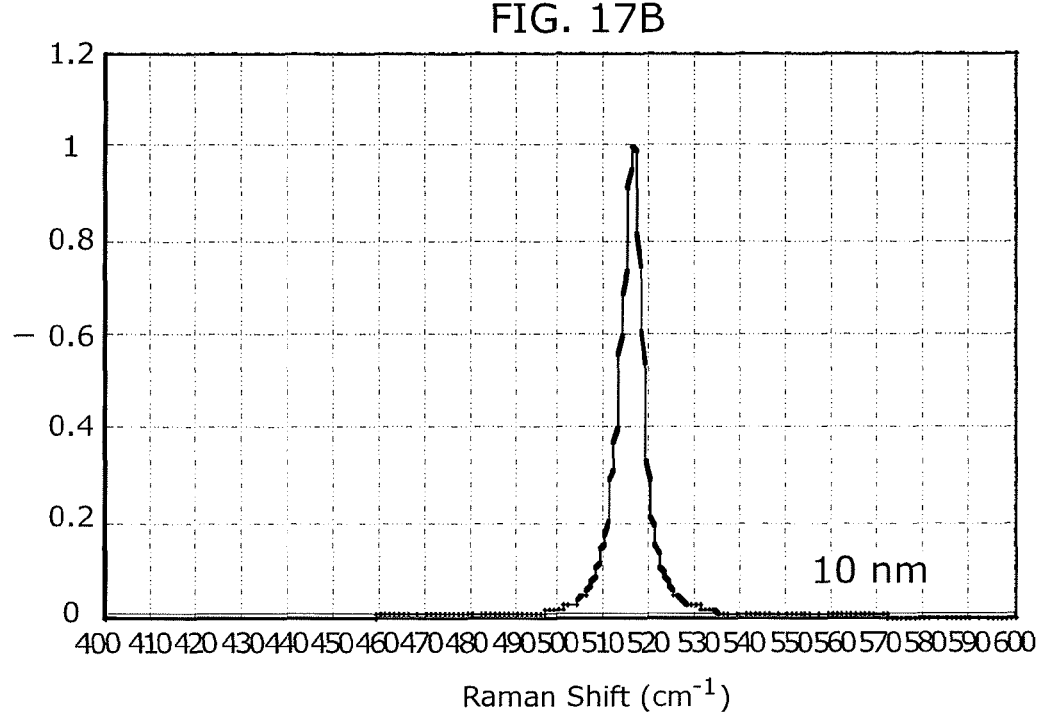
FIG. 17B is a graph plotting a result of calculating a Raman spectrum dependency of a coherence length of a phonon according to Embodiment 2.
Figure 17C:
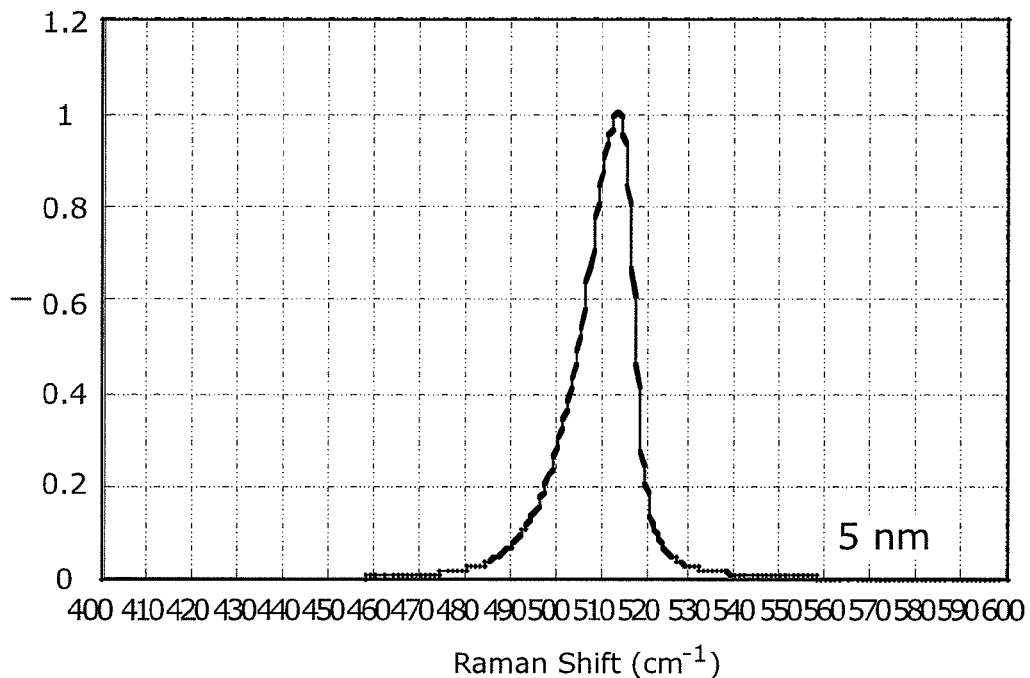
FIG. 17C is a graph plotting a result of calculating a Raman spectrum dependency of a coherence length of a phonon according to Embodiment 2.
Figure 17D:
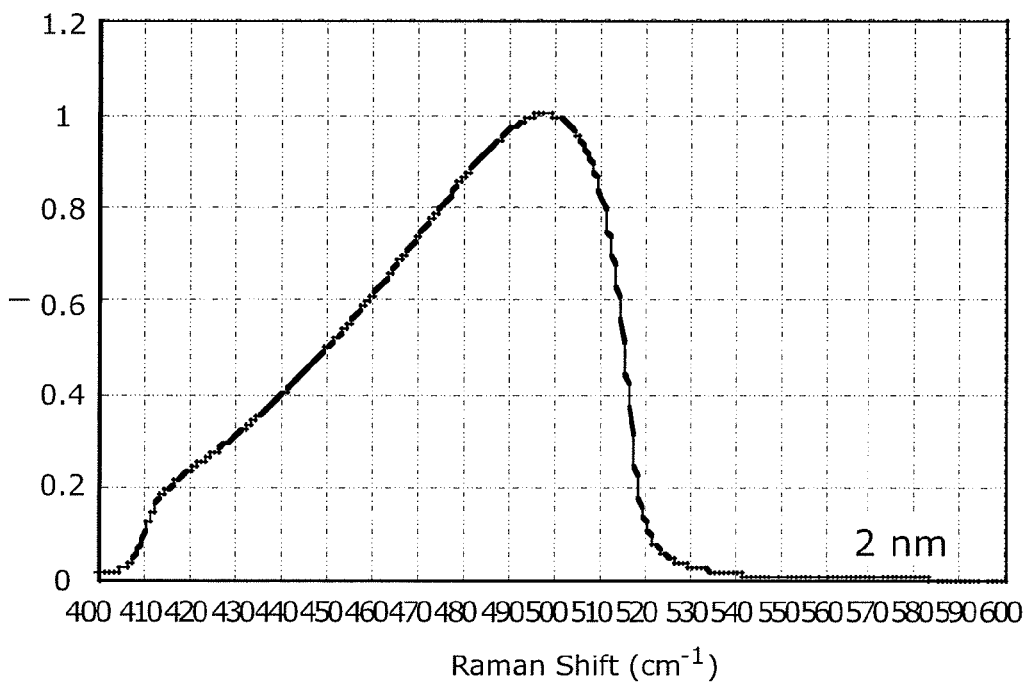
FIG. 17D is a graph plotting a result of calculating a Raman spectrum dependency of a coherence length of a phonon according to Embodiment 2.
Figure 17E:
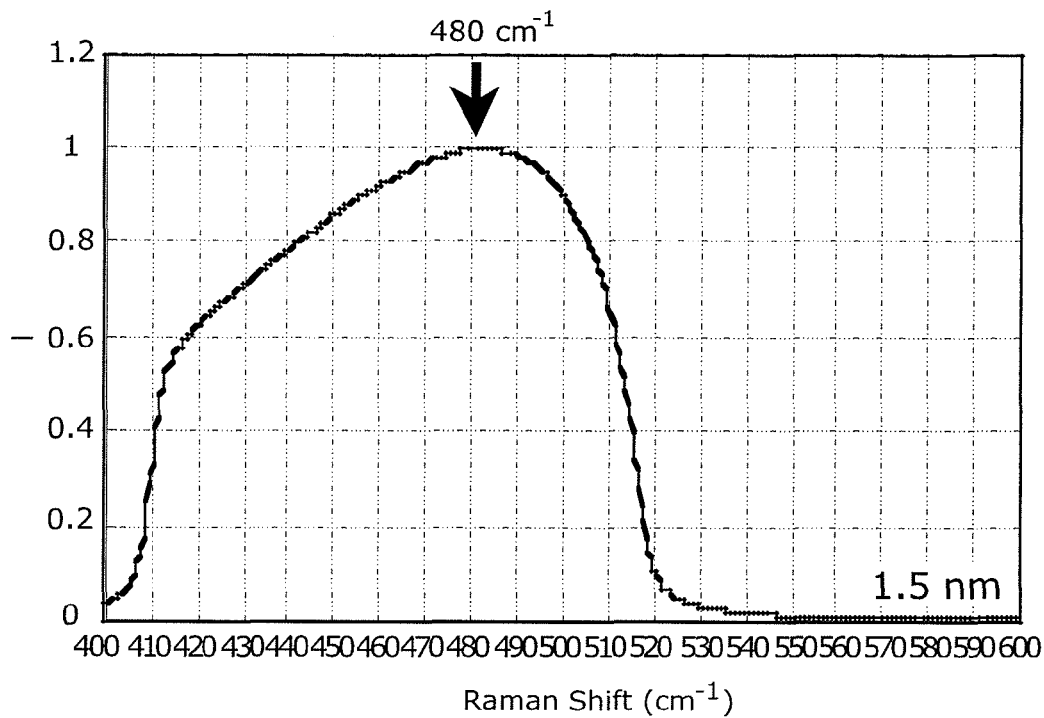
FIG. 17E is a graph plotting a result of calculating a Raman spectrum dependency of a coherence length of a phonon according to Embodiment 2.
Figure 17F:
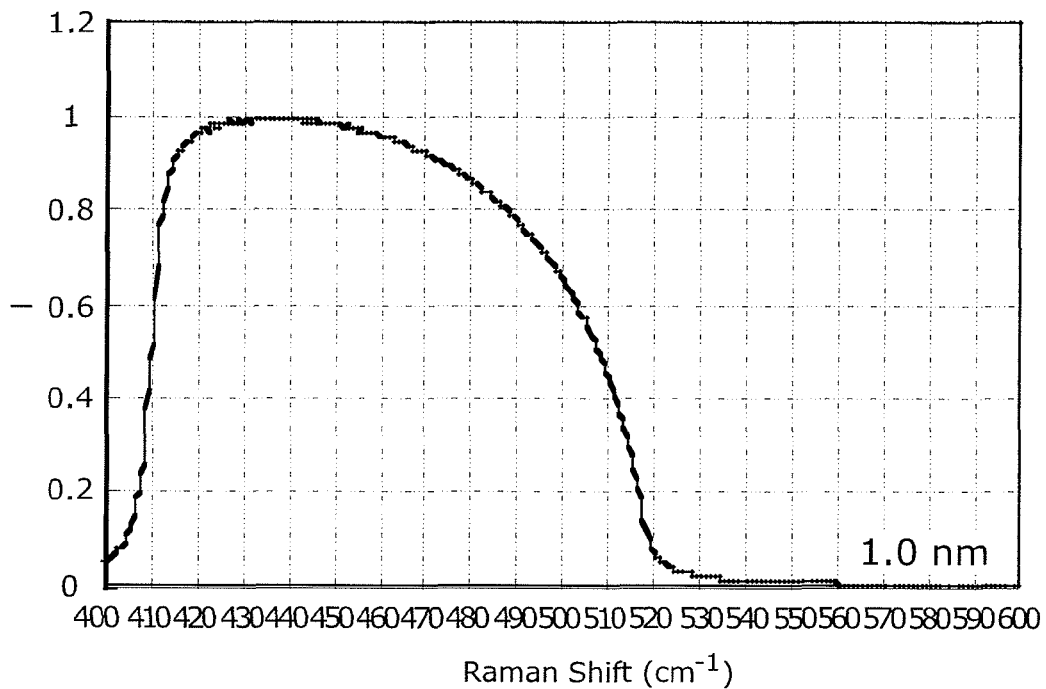
FIG. 17F is a graph plotting a result of calculating a Raman spectrum dependency of a coherence length of a phonon according to Embodiment 2.

FIG. 16 is a flowchart for explaining an analysis method of a Raman spectrum used in the film quality analysis method for a crystalline semiconductor film according to the present embodiment.

Figure 26:
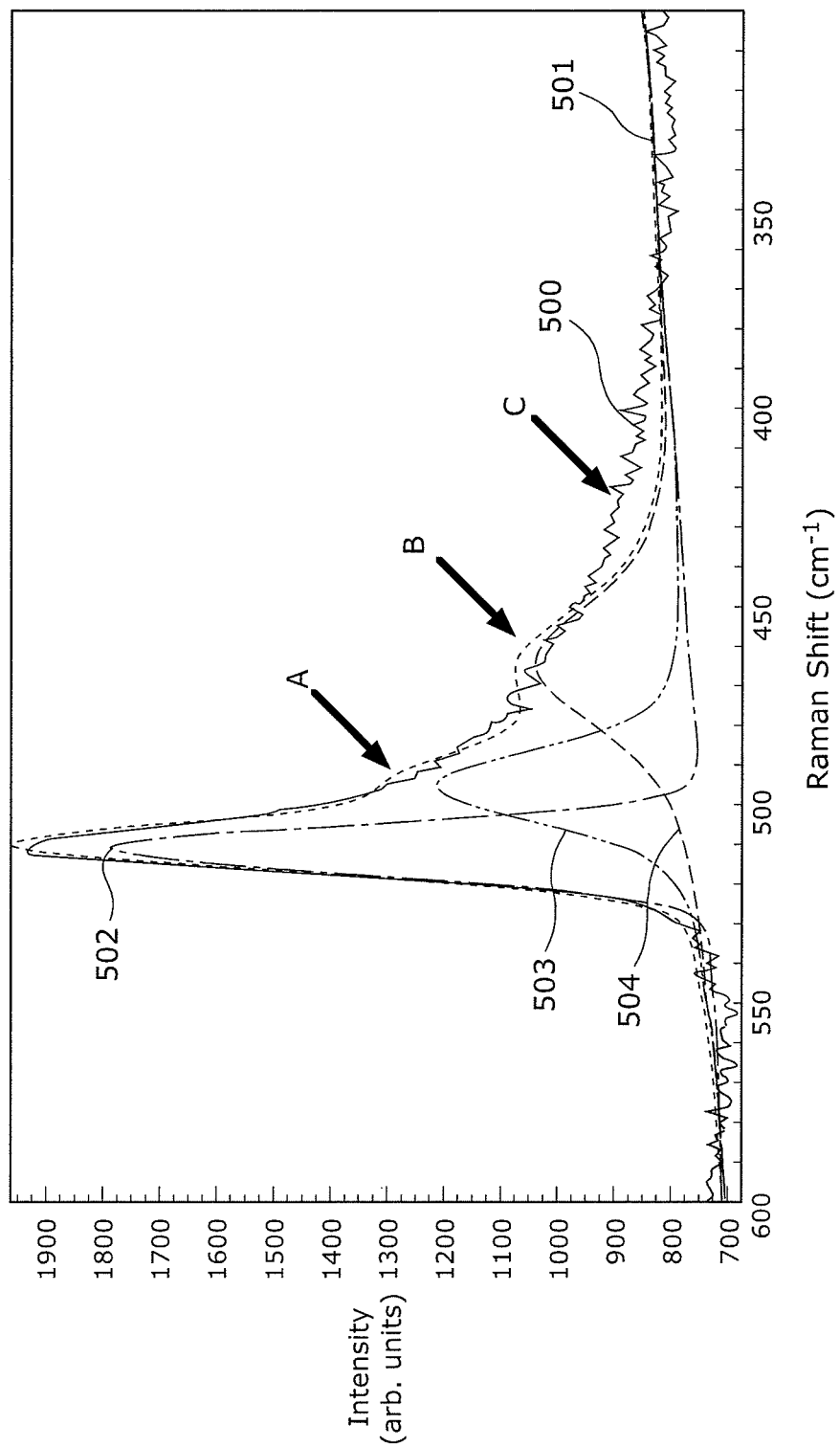
FIG. 26 is a graph plotting a Raman spectrum of a crystalline silicon film and an analysis result by a conventional analysis method.

First, a Raman spectrum is measured by using the Raman spectrometer 200 (S301). More specifically, a peak waveform of a Raman band corresponding to a phonon mode unique to a crystalline semiconductor film is measured by Raman spectrometry. For example, as shown in FIG. 26, regarding the crystalline silicon film as a crystalline semiconductor film, a Raman peak corresponding to a phonon unique to a silicon film is observed in a range from 450 cm$^{-1}$ to 550 cm$^{-1}$. As described above, a Raman peak unique to a crystalline silicon film is observed at 520 cm$^{-1}$, a Raman peak unique to a microcrystalline silicon film is observed in a range approximately from 500 cm$^{-1}$ to 510 cm$^{-1}$, and a Raman peak unique to an a-Si film is observed at approximately 480 cm$^{-1}$. In the embodiment described below, a Raman peak observed in the above-described region is analyzed by using the analysis method according to the present embodiment.

Next, a baseline of a measured Raman spectrum is corrected (S302). More specifically, after measuring a peak waveform, a baseline of the peak waveform is corrected. For example, the baseline is corrected by using a method of performing straight-line approximation on the region for which the Raman spectrum has been analyzed. This is because the baseline of the Raman spectrum is sometimes inclined affected by the sample (here, the specimen 307) or the measurement environments. This is seen, for example, in FIG. 26 where a baseline is inclined due to incident light (Rayleigh light). There is the case where the baseline is not inclined. In this case, it is not necessary to correct the baseline.

Next, fitting is performed on a Raman spectrum by using a Raman intensity function (Raman spectrum function) (S303).

More specifically, a Raman peak waveform analysis model is generated, and a peak waveform is reproduced by using the generated Raman peak waveform analysis model. Although more detail description will be given later, the fitting on a Raman spectrum (reproduction of the Raman spectrum) is performed by analyzing the Raman spectrum, assuming that the Raman spectrum having the corrected baseline has three components of a crystalline silicon component, a microcrystalline silicon component, an a-Si component.

Next, based on the results of fitting the Raman spectrum, parameters are extracted (S304). More specifically, from the Raman peak waveform analysis model obtained by spectrum analysis, a peak position, a FWHM, a peak intensity, a volume fraction, and the like of each component are extracted as parameters.

As described above, the Raman spectrum obtained by the Raman spectrometer 200 is analyzed.

Next, the above-described method of analyzing a Raman spectrum at S303 is described in more detail.

Conventionally, analysis has been performed under assumption that a function expressing dispersion of each unique phonon can be expressed by using Gauss function, Lorenz function, or a complex function (Voit function) of these functions. On the other hand, according to the present embodiment, analysis is performed by using a Raman spectrum function in consideration of a coherence length of a phonon as the function expressing dispersion of each unique phonon. The following Equations 1 and 2 express a Raman spectrum function used in the present embodiment.

$$I(\omega) = C \int_0^{2\pi} d\varphi \int_{-\pi}^{\pi} \sin\theta \, d\theta \int_0^1 \left[ \frac{f(q)}{[\omega - \omega(q)]^2 + \left(\frac{\Gamma_0}{2}\right)^2} \right] q^2 \, dq \quad \text{(Equation 1)}$$

$$f(q) = \exp\left(-\frac{q^2 L c^2}{4a}\right) \quad \text{(Equation 2)}$$

where Lc denotes a phonon coherence length, a denotes a lattice constant (crystalline silicon: 0.53 nm), $\Gamma_0$ denotes a FWHM of a Raman peak of crystalline silicon (depending on a measuring system), C denotes a normalization constant, and f(q) denotes a weighting function.

Normally, since Raman scattering is inelastic scattering of light, only a Raman peak (520.6 cm$^{-1}$) of a TO phonon is observed when kinetic energy is 0 according to the selection rule. However, if crystallinity of the crystalline silicon film is deteriorated, the above-described selection rule does not work, and other phonon modes become also Raman activity and are therefore observed to some extent.

Each of FIGS. 17A to 17F is a graph plotting a result of calculating a Raman spectrum dependency of a coherence length of a phonon according to Embodiment 2. In the figures, a vertical axis indicates a normalized Raman peak intensity, and a horizontal axis indicates a Raman shift (difference from incident light). FIGS. 17A to 17F show results of calculating a Raman spectrum by varying Lc to 50 nm, 10 nm, 5 nm, 2 nm, 1.5 nm, 1 nm, and 0 nm, respectively.

It is known that a coherence length of a phonon is restricted in a system where crystal is deteriorated or a phonon is confined. It is also seen in the results of FIGS. 17A to 17F that as Lc is decreased, a FWHM of a Raman peak is increased and a peak position shifts to a lower frequency. It is also seen that when Lc is equal to or less than 5 nm, a shape of the Raman spectrum depends heavily on Lc.

Therefore, a Raman spectrum function of each of an a-Si component, a microcrystalline silicon component, and a crystalline silicon component can be characterized by a corresponding phonon coherence length. Therefore, a Raman spectrum of a measured crystalline silicon film can be expressed by the following Equations 3 and 4.

$$I(\omega) = \sigma_a Ia(\omega) + \sigma_{mc} I\mu c(\omega) + \sigma_c Ic(\omega) \quad \text{(Equation 3)}$$

where $$\sigma_a + \sigma_{mc} + \sigma_c = 1 \quad \text{(Equation 4)}$$

where $\sigma_a$, $\sigma_{mc}$, and $\sigma_c$ denote volume fractions of an a-Si component, a microcrystalline silicon component, and a crystalline silicon component, respectively, and $Ia(\omega)$, $I\mu c(\omega)$, and $Ic(\omega)$ are Raman spectrum functions of an a-Si component, a microcrystalline silicon component, and a crystalline silicon component, respectively.

From the above, at S303, first, $Ic(\omega)$ is a Raman band of a crystalline silicon component, $I\mu c(\omega)$ is a Raman band of a microcrystalline silicon component, $Ia(\omega)$ is a Raman band of an amorphous silicon component, $\sigma_c$ is a volume fraction of a crystalline silicon component, $\sigma_{mc}$ is a volume fraction of a microcrystalline silicon component, and $\sigma_a$ is a volume fraction of an amorphous silicon component. Subsequently, the step S303 includes the following first to three processes. In the first process, a Raman peak waveform analysis model expressed by Equation 3 is generated. In the second process, a Raman band of a crystalline silicon component, a Raman band of a microcrystalline silicon component, a Raman band of an amorphous silicon component are described by the Raman spectrum function determined by Equation 2, where Lc denotes a phonon coherence length, a denotes a lattice constant, $\Gamma_0$ denotes a FWHM of a Raman peak of a monocrystalline semiconductor, and C denotes a normalized constant. In the third process, a Raman peak waveform analysis model is used by using the above-described Raman spectrum function, and the peak waveform is reproduced by using the generated Raman peak waveform analysis model. By the first to third processes, fitting on the Raman spectrum (reproduction of the peak waveform) is performed by using the Raman spectrum function.

Therefore, in the analysis method according to the present embodiment, fitting is performed on an experimental result (Raman spectrum) by using a phonon coherence length and a volume fraction of each of the components as parameters. Then, parameters such as a peak position, a FWHM, and a crystallization ratio are extracted.

Here, a crystallization ratio is used as an index indicating a film quality of a crystalline silicon film, and defined as the following Equation 5.

$$\text{Crystallization Ratio} = \sigma_{mc} + \sigma_c \quad \text{(Equation 5)}$$

Next, the description is give for Examples where crystalline silicon films manufactured by various techniques are analyzed by using the above-described analysis method according to the present embodiment.

Example 1

According to the present example, a result of analyzing a Raman spectrum of a crystalline silicon film manufactured by crystallizing an a-Si film by using continuous wave (CW) laser is described.

A specimen (specimen 307) is generated by forming a silicon nitride film (base coat layer) of approximately 200 nm and an a-Si film of approximately 50 nm on a glass substrate, and then crystallizing them by CW laser. The a-Si crystallization is performed by using CW laser with a wavelength of 532 nm and a power density of 70 Kw/cm$^2$.

Here, as a plurality of such specimens 307, samples for which a scan speed of the laser is varied to vary the crystalline structure are manufactured. In more detail, samples having respective crystalline silicon films for which solid-phase growth, partial-melt growth, and melt growth are performed, respectively. Here, in order to form crystalline silicon films for which solid-phase growth, partial partial-melt growth, and melt growth are performed, respectively, laser is irradiated to each of the samples at different scan speeds of 440 mm/s, 360 mm/s, and 260 mm/s, respectively.

Figure 18A:
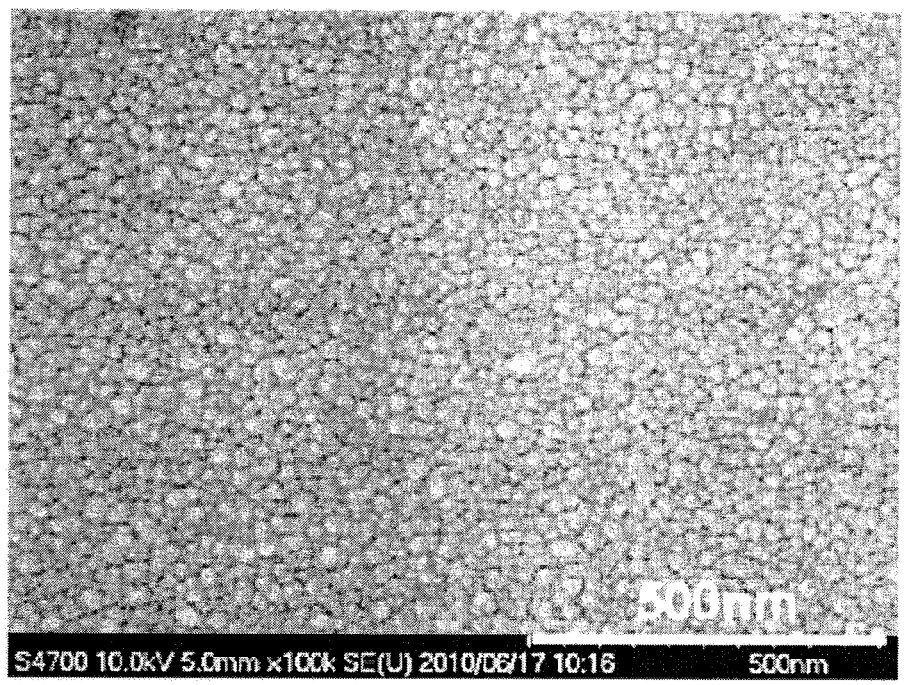
FIG. 18A is a diagram showing a Raman spectrum of a solid-phase grown crystalline silicon film and its analysis result according to Example 1 of Embodiment 2.
Figure 18B:
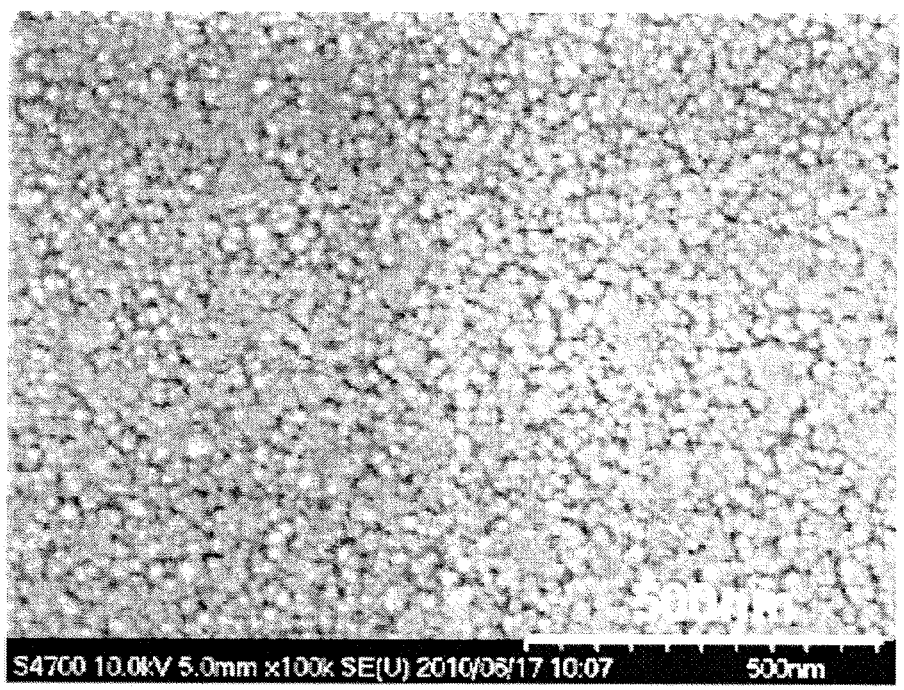
FIG. 18B is a diagram showing a Raman spectrum of a partial-melt grown crystalline silicon film and its analysis result according to Example 1 of Embodiment 2.
Figure 18C:
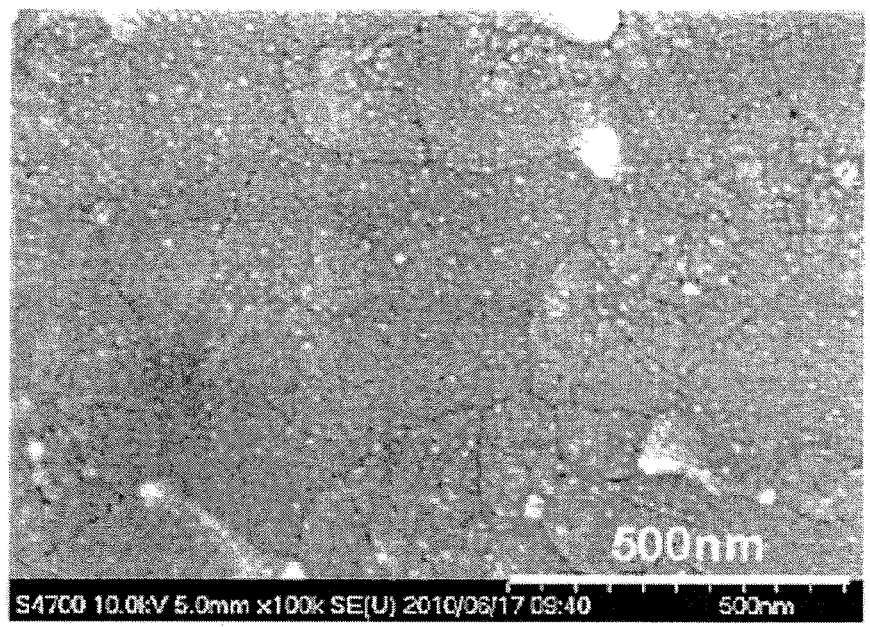
FIG. 18C is a diagram showing a Raman spectrum of a melt-grown crystalline silicon film and its analysis result according to Example 1 of Embodiment 2.

Each of FIGS. 18A to 18C is a diagram showing an image of a corresponding one of the crystalline silicon films which is produced by a planar electronic microscope (SEM) in Example 1. FIGS. 18A to 18C are SEM images of the crystalline silicon films for which solid-phase growth, partial-melt growth, and melt growth are performed, respectively, by using the above-described method. It is seen in FIG. 18A that the solid-phase grown crystalline silicon is observed to have a grain size of approximately 30 nm. It is seen in FIG. 18B that the partial-melt grown crystalline silicon film is observed to have a grain size ranging approximately from 40 nm to 50 nm. It is seen in FIG. 18C that the melt grown crystalline silicon is observed to have a grain size ranging approximately from 100 nm to 200 nm.

Figure 19:
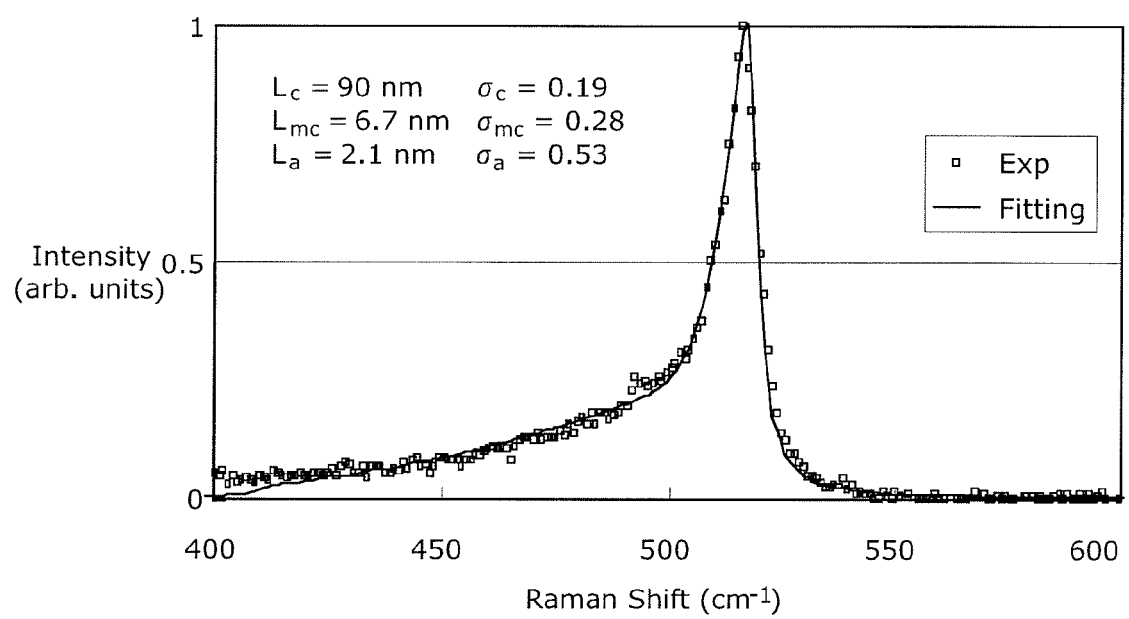
FIG. 19 is a graph plotting a Raman spectrum of a solid-phase grown crystalline silicon film and its analysis result according to Example 1 of Embodiment 2.
Figure 20:
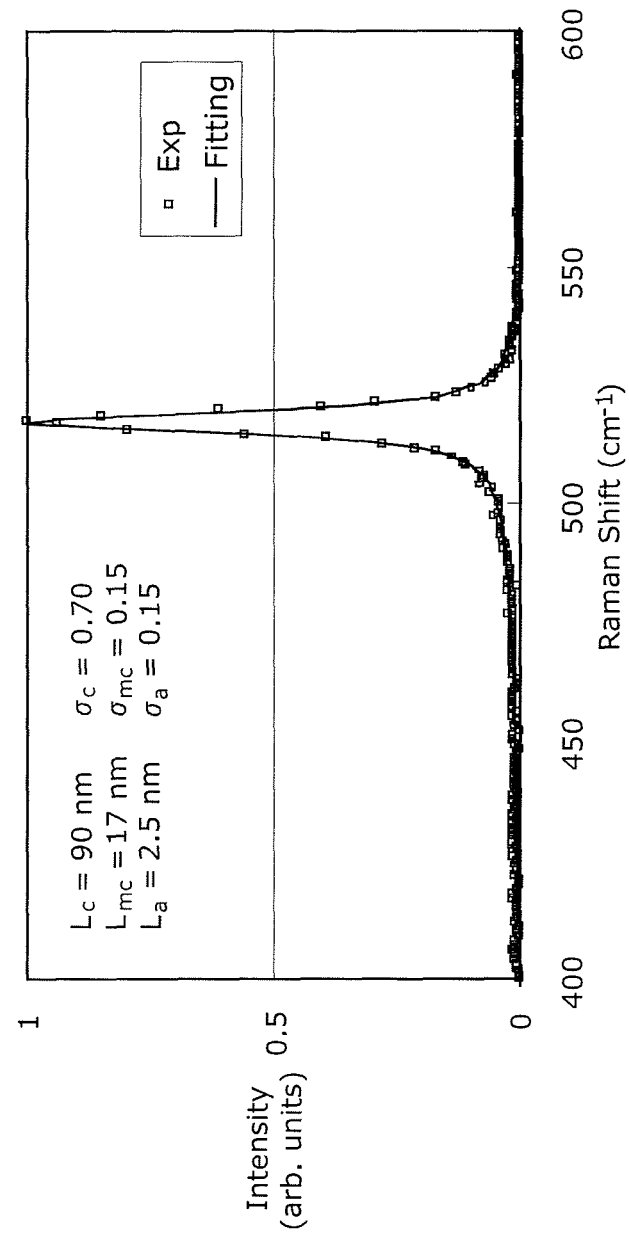
FIG. 20 is a graph plotting a Raman spectrum of a partial-melt grown crystalline silicon film and its analysis result according to Example 1 of Embodiment 2.
Figure 21:
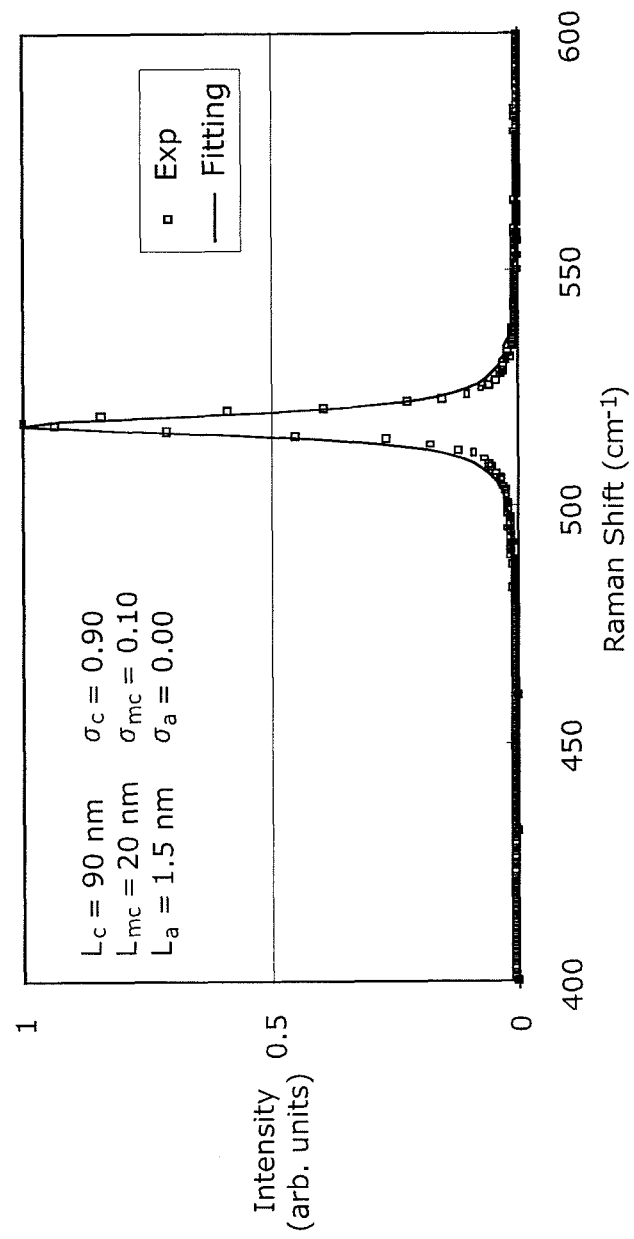
FIG. 21 is a graph plotting a Raman spectrum of a melt-grown crystalline silicon film and its analysis result according to Example 1 of Embodiment 2.

FIG. 19 is a graph plotting a Raman spectrum of the solid-phase grown crystalline silicon film and its analysis result according to Example 1. FIG. 20 is a graph plotting a Raman spectrum of the partial-melt grown crystalline silicon film and its analysis result according to Example 1. FIG. 21 is a graph plotting a Raman spectrum of the melt grown crystalline silicon film and its analysis result according to Example 1.

It is seen in FIGS. 19 to 21 that crystallization ratios of the solid-phase grown crystalline silicon film, the partial-melt grown crystalline silicon film, and the melt grown crystalline silicon film are 43%, 85%, and 100%, respectively. The results qualitatively match the respective crystallinity confirmed in FIGS. 18A to 18C.

Moreover, as shown in FIGS. 19 to 21, when the measuring results are compared to the analysis results, these results mach each other more in the analysis method according to the present embodiment than in the conventional analysis method. In particular, it is conformed that the fitting accuracy for lower frequency is considerably increased. This is because a spectrum of each component is weighted by a phonon coherence length as determined by the above-presented Equation 3, so that spattering of each component can be asymmetrical with regard to a frequency. Furthermore, since a spectrum of each component is influenced by a coherence length that is a physicality value, there is physical meaning.

Figure 22:
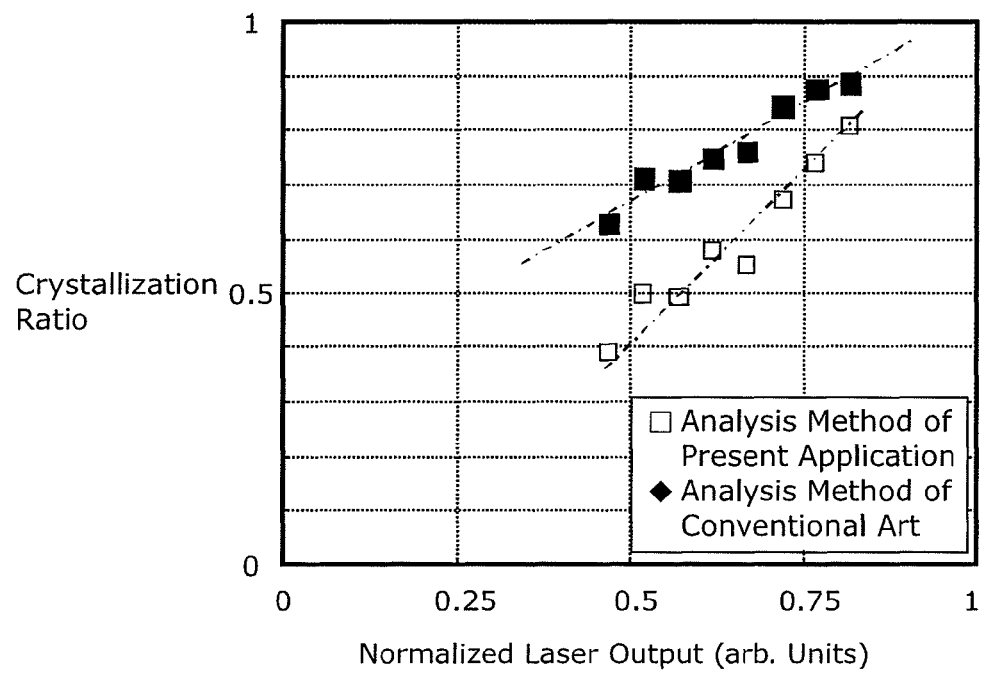
FIG. 22 is a graph comparing (a) a crystallization ratio of a crystalline silicon film retrieved by the analysis method according to Embodiment 2 to (b) a crystallization ratio of a crystalline silicon film retrieved by a conventional analysis method.

FIG. 22 is a graph comparing (a) a crystallization ratio of a crystalline silicon film retrieved by the analysis method according to the present embodiment to (b) a crystallization ratio of a crystalline silicon film retrieved by the conventional analysis method. In FIG. 22, a vertical axis indicates a crystallization ratio retrieved by Raman spectrum analysis, and a horizontal axis indicates a normalized laser output. FIG. 22 plots a crystallization ratio extracted from a Raman spectrum by using the analysis method according to the present embodiment, and a crystallization ratio extracted from the same Raman spectrum by using the conventional analysis method (assuming that spattering of each component is Gauss function).

In laser crystallization, it is known that a crystal grain size is increases as a laser output is increased. It is also seen in FIG. 22 that the crystallization ratio is increased as the laser output is increased. In view of the above, the analysis method according to the present embodiment estimates a crystallization ratio lower and has sharper inclination with regard to a laser output, in other words, has more sensitivity to crystallinity, in comparison to the conventional analysis method.

As seen in the above-described results, the analysis method according to the present embodiment can more correctly analyze a Raman spectrum of a crystalline silicon film. Therefore, the obtained parameters are physically more efficient than the conventional ones. In addition, it is possible to analyze crystallinity of a crystalline silicon film at a higher sensitivity. Therefore, as known from the present example, by using the obtained parameters, it is possible to more correctly manage a film quality of a crystalline silicon film.

Example 2

According to the present example, a result of analyzing a Raman spectrum of a crystalline silicon film manufactured by crystallizing an a-Si film by using Rapid Thermal Annealing (RTA).

A specimen (specimen 307) is generated by forming a silicon nitride film (base coat layer) of approximately 200 nm and an a-Si film of approximately 50 nm on a quartz substrate, and then crystallizing them by RTA. The a-Si crystallization is performed at 750° C. for 5 minutes. In the present example, crystallinity of the crystalline silicon film can be controlled by controlling an annealing temperature, a retention time duration, a cooling speed, and the like, although they are not shown.

FIG. 23 is a diagram showing an image of the crystalline silicon film which is produced by a planar electronic microscope (SEM) in Example 2. FIG. 23 shows the crystalline silicon film crystallized by using the above-described RTA. The crystalline silicon film shown in FIG. 23 is a partial-melt grown crystal, and it is seen that the crystalline silicon film has a grain size ranging approximately 40 nm to 50 nm.

Figure 24:
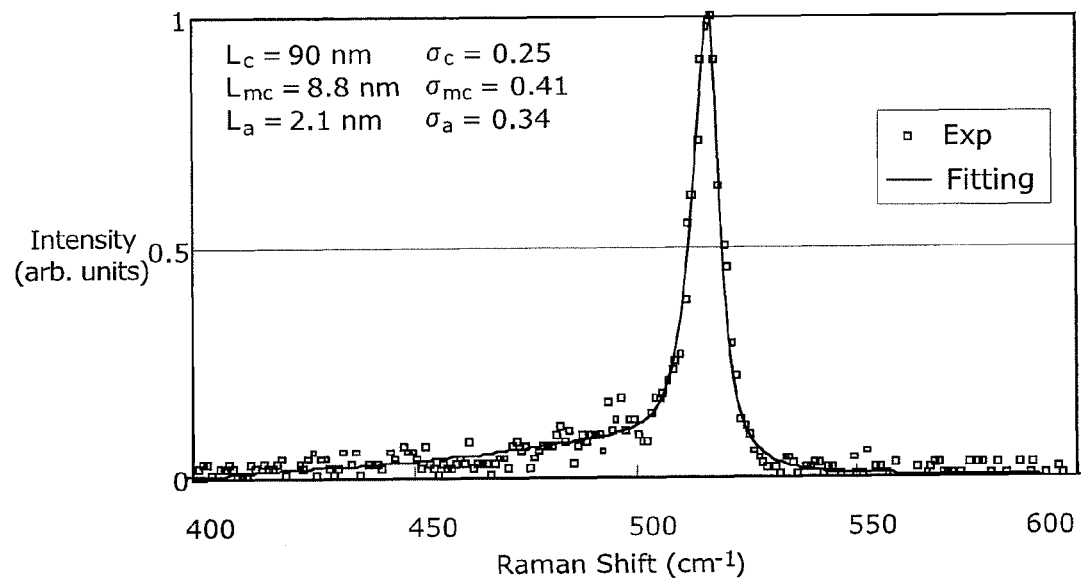
FIG. 24 is a graph plotting a Raman spectrum of a crystalline silicon film crystallized by a RTA method and its analysis result according to Example 2 of Embodiment 2.
Figure 25:
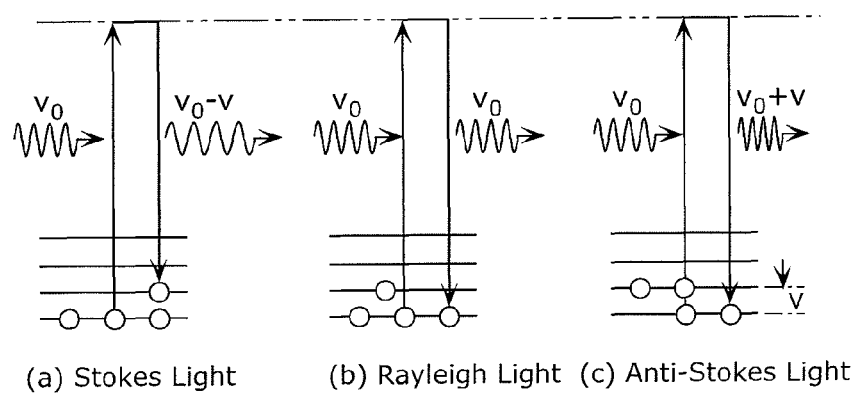
FIG. 25 is a diagram schematically showing Raman scattering by incident light and molecular energy exchange.

FIG. 24 is a graph plotting a Raman spectrum of the crystalline silicon film crystallized by the RTA and its analysis result according to Example 2. It is learned from the analysis results shown in FIG. 24 that the crystallization ratio of the crystalline silicon film is 66%. In FIG. 24, when the measuring results are compared to the analysis results, these results mach each other more in the analysis method according to the present embodiment than in the conventional analysis method.

The crystalline silicon film is known as having different crystalline structure depending on a crystallization method. Therefore, there is a high possibility that a crystallization ratio of a partial-melt grown crystalline silicon film formed by RTA in the present example is different from a crystallization ratio of the crystalline silicon film (crystalline structure) of Example 1 because the crystallization techniques are different.

As seen in the above-described results, the analysis method according to the present embodiment can more correctly analyze also a Raman spectrum of a crystalline silicon film manufacture by RTA.

Therefore, as known from the present example, by using the obtained parameters, it is possible to more correctly manage a film quality of a crystalline silicon film.

Thus, according to the present embodiment, since a model based on a physical status of a film quality of a crystalline semiconductor film can be used, it is possible to implement a film quality analysis method for a crystalline semiconductor film for which a film quality of a crystalline semiconductor film can be correctly evaluated and analyzed.

More specifically, at phonon modes of crystalline silicon, microcrystalline silicon, and a-Si, a spectrum separation method using a Raman spectrum function in consideration of a phonon coherence length is used to improve reproducibility of an experimental spectrum. Furthermore, by using a model based on a physical status, reliability of extracted parameters is increased to enable correct evaluation and analysis for crystallinity.

It should be noted that the film quality analysis method for a crystalline semiconductor film according to the present embodiments is not limited to the present embodiments. Those skilled in the art will be readily appreciated that various modifications and combinations of the structural elements and functions in the embodiments are possible without materially departing from the novel teachings and advantages of the present disclosure. Accordingly, all such modifications and combinations are intended to be included within the scope of this disclosure.

For example, in the film quality analysis method for a crystalline semiconductor film according to the present embodiment, a generated Raman spectrum function may be used in the crystallinity evaluation method according to Embodiment 1. For example, in the crystallinity evaluation method and the crystallinity evaluation computer software according to the present embodiment, it is possible to perform fitting on a Raman spectrum by a Raman spectrum function by using an extracted peak value. The Raman spectrum function is not Lorenz function itself, but is a function described by Lorenz function. Therefore, as S204, it is also possible to perform fitting on a Raman spectrum by using a Raman spectrum function not by using Lorenz function itself, so that the aspect is also included in the scope of the present disclosure.

More specifically, the crystallinity evaluation method for evaluating crystallinity of a semiconductor film formed on a substrate may include the following steps: measuring a Raman spectrum of the semiconductor film by Raman spectrometry so as to obtain a peak waveform of a Raman band corresponding to a phonon mode unique to the semiconductor film, the peak waveform being a waveform of a wavelength range having a peak of the Raman band; generating a waveform by fitting the obtained peak waveform of the Raman band by using a Raman spectrum function described by a Lorenz function based on the peak waveform, the waveform being a waveform fit by the Raman spectrum function; obtaining at least one of a peak value, a FWHM, and a wavelength indicating the peak value regarding the generated waveform; and evaluating crystallinity of the semiconductor film based on the at least one of the peak value, the FWHM, and the wavelength indicating the peak value, wherein the generating of the waveform includes: generating a Raman peak waveform analysis model expressed by Equation 3, where $Ic(\omega)$ denotes a Raman band of a crystalline silicon component, $I\mu c(\omega)$ denotes a Raman band of a microcrystalline silicon component, $Ia(\omega)$ denotes a Raman band of an amorphous silicon component, $\sigma_c$ denotes a volume fraction of the crystalline silicon component, $\sigma_{mc}$ denotes a volume fraction of the microcrystalline silicon component, and $\sigma_a$ denotes a volume fraction of the amorphous silicon component; and describing each of the Raman band of the crystalline silicon component, the Raman band of the microcrystalline silicon component, and the Raman band of the amorphous silicon component, by using the Raman spectrum function as expressed by Equations 1 and 4, where Lc denotes a phonon coherence length, a denotes a lattice constant, $\theta_0$ denotes a FWHM of a Raman peak of a monocrystalline semiconductor, and C denotes a normalized constant.

Furthermore, for example, according to the present embodiment, in the above-described method of analyzing a Raman spectrum, a Raman band waveform of a crystalline semiconductor film is analyzed, but this analysis may be performed by using a computer. Therefore, a computer software having a program for analyzing a Raman band waveform obtained by Raman spectroscopy in order to perform film quality analysis for a crystalline semiconductor film formed on a substrate according to the present embodiment is also included in the present disclosure.

Furthermore, according to the present embodiment, a Raman band waveform of a crystalline semiconductor film is analyzed by the above-described Raman spectrum analysis method, but it is possible to manage a film quality of a crystalline semiconductor film by using parameters extracted results of the analysis. Therefore, a method of analyzing a film quality of a crystalline semiconductor film formed on a substrate according to the embodiment and managing steps of device processes is also included in the present disclosure.

As a result, a method of speedily managing a film quality inline by using the computer software having the analysis method according to the present embodiment and this analysis method can be implemented.

Thus, according to the present embodiments, since a model based on a physical status of a film quality of a crystalline semiconductor film can be used, it is possible to implement a film quality analysis method and film quality analysis computer software which are capable of correctly evaluating and analyzing a film quality of a crystalline semiconductor film, and a method of managing the film quality analysis method and the computer software.

In this way, it is possible to implement a crystallinity evaluation method and a crystallinity evaluation device each capable of correctly evaluating crystallinity of a crystalline semiconductor film having high-mobility characteristics without mobility variation, and a computer software for them.

Although the crystallinity evaluation method, the crystallinity evaluation device, and the computer software thereof according to the present disclosure have been described with reference to the embodiments as above, the present disclosure is not limited to these embodiments. Those skilled in the art will be readily appreciated that various modifications and combinations of the structural elements and functions are possible in the embodiments without materially departing from the novel teachings and advantages of the present disclosure. Such modifications and combinations are also embodiments of the present disclosure.

Each of the structural elements in each of the above-described embodiments may be configured in the form of an exclusive hardware product, or may be realized by executing a software program suitable for the structural element. Each of the structural elements may be realized by means of a program executing unit, such as a CPU and a processor, reading and executing the software program recorded on a recording medium such as a hard disk or a semiconductor memory. Here, the software program for realizing the image decoding apparatus according to each of the embodiments is a computer software described below.

The computer software is recorded on a computer-readable recording medium, the computer software evaluating crystallinity of a crystalline semiconductor film, wherein the computer software includes a program causing a computer to execute the crystallinity evaluation method according to any one of Claims 1 to 7 to output a result of the evaluation of the crystallinity of the semiconductor film.

The herein disclosed subject matter is to be considered descriptive and illustrative only, and the appended Claims are of a scope intended to cover and encompass not only the particular embodiment(s) disclosed, but also equivalent structures, methods, and/or uses.

INDUSTRIAL APPLICABILITY

The crystallinity evaluation method, the crystallinity evaluation device, and the computer software thereof according to one or more exemplary embodiments disclosed herein are applicable, in particular, to crystallinity evaluation methods, crystallinity evaluation devices, and computer software thereof for correctly evaluating crystallinity of a crystalline silicon film in manufacturing TFTs to be used in display devices and the like such as liquid crystal displays and organic EL television sets.

The invention claimed is:

1. A crystallinity evaluation method of evaluating crystallinity of a semiconductor film formed above a substrate, the crystallinity evaluation method comprising:
   obtaining a peak waveform of a Raman band in a Raman spectrum of the semiconductor film using Raman spectrometry, the Raman band corresponding to a phonon mode unique to the semiconductor film, the peak waveform being a waveform of a wavelength range having a peak of the Raman band;
   generating a first waveform by fitting the obtained peak waveform of the Raman band by using a Gauss function, the first waveform being a waveform fit by the Gauss function;
   extracting a peak value of the first waveform;
   generating a second waveform by fitting the obtained peak waveform of the Raman band by using a Lorenz function based on the extracted peak value, the second waveform being a waveform fit by the Lorenz function;
   obtaining at least one of a peak value, a full-width at half maximum, and a wavelength indicating the peak value regarding the generated second waveform; and
   evaluating crystallinity of the semiconductor film based on the at least one of the peak value, the full-width at half maximum, and the wavelength indicating the peak value.

2. The crystallinity evaluation method according to claim 1,
   wherein the crystallinity of the semiconductor film is evaluated by comparing (a) the at least one of the peak value, the full-width at half maximum, and the wavelength indicating the peak value to (b) at least one of a reference peak value, a reference full-width at half maximum, and a wavelength indicating the reference peak value which are previously stored in a lookup table,
   in the lookup table, as the at least one of the reference peak value, the reference full-width at half maximum, and the wavelength indicating the reference peak value, at least one of a peak value, a full-width at half maximum, and a wavelength indicating the peak value regarding a third waveform is previously stored, the third waveform being generated prior to the obtaining of the peak waveform of the Raman band by fitting a peak waveform of a Raman band corresponding to a phonon mode unique to the crystalline semiconductor film by using the Lorenz function, and
   in the lookup table, a result of the evaluation of the crystallinity of the crystalline semiconductor film which includes a crystal grain size, an existence ratio of a crystal grain, and a mobility is stored in association with the at least one of the reference peak value, the reference full-width at half maximum, and the wavelength indicating the reference peak value.

3. The crystallinity evaluation method according to claim 1,
  wherein the evaluating of the crystallinity of the semiconductor film includes determining whether or not the full-width at half maximum is in a range from $5.0 \text{ cm}^{-1}$ to $6.0 \text{ cm}^{-1}$, so as to evaluate the crystallinity of the semiconductor film.

4. The crystallinity evaluation method according to claim 1,
  wherein the semiconductor film is made of silicon, and
  the evaluating of the crystallinity of the semiconductor film includes determining whether or not a ratio of the full-width at half maximum to a full-width at half maximum of a Raman band of monocrystalline silicon is in a range from 1.5 to 1.8, so as to evaluate the crystallinity of the semiconductor film.

5. The crystallinity evaluation method according to claim 1,
  wherein the semiconductor film is made of silicon, and
  the evaluating of the crystallinity of the semiconductor film includes determining whether or not a difference between the full-width at half maximum and a full-width at half maximum of a Raman band of the monocrystalline silicon is in a range from $1.8 \text{ cm}^{-1}$ to $2.4 \text{ cm}^{-1}$, so as to evaluate the crystallinity of the semiconductor film.

6. The crystallinity evaluation method according to claim 1,
  wherein the evaluating of the crystallinity of the semiconductor film includes determining whether or not a ratio of the peak value to a full-width at half maximum of a Raman band of crystalline silicon is in a range from 0.1 to 0.2, so as to evaluate the crystallinity of the semiconductor film.

7. A method of manufacturing a semiconductor film by evaluating crystallinity of a crystalline semiconductor film by using the crystallinity evaluation method according to claim 1 so as to select the crystalline semiconductor film having predetermined crystallinity.

8. The crystallinity evaluation method according to claim 1, further comprising:
  performing, with a spectrometer, the Raman spectrometry on the semiconductor film to obtain the Raman spectrum of the semiconductor film.

9. A non-transitory computer-readable recording medium including executable instructions for evaluating crystallinity of a semiconductor film formed above a substrate, the executable instructions, when executed by a computer, causing the computer to perform operations to output a result of the evaluating of the crystallinity of the semiconductor film, the operations comprising:
  obtaining a peak waveform of a Raman band in a Raman spectrum of the semiconductor film using Raman spectrometry, the Raman band corresponding to a phonon mode unique to the semiconductor film, the peak waveform being a waveform of a wavelength range having a peak of the Raman band;
  generating a first waveform by fitting the obtained peak waveform of the Raman band by using a Gauss function, the first waveform being a waveform fit by the Gauss function;
  extracting a peak value of the first waveform;
  generating a second waveform by fitting the obtained peak waveform of the Raman band by using a Lorenz function based on the extracted peak value, the second waveform being a waveform fit by the Lorenz function;
  obtaining at least one of a peak value, a full-width at half maximum, and a wavelength indicating the peak value regarding the generated second waveform; and
  evaluating crystallinity of the semiconductor film based on the at least one of the peak value, the full-width at half maximum, and the wavelength indicating the peak value.

10. The non-transitory computer-readable recording medium according to claim 9,
  wherein the crystallinity of the semiconductor film is evaluated by comparing (a) the at least one of the peak value, the full-width at half maximum, and the wavelength indicating the peak value to (b) at least one of a reference peak value, a reference full-width at half maximum, and a wavelength indicating the reference peak value which are previously stored in a lookup table,
  in the lookup table, as the at least one of the reference peak value, the reference full-width at half maximum, and the wavelength indicating the reference peak value, at least one of a peak value, a full-width at half maximum, and a wavelength indicating the peak value regarding a third waveform is previously stored, the third waveform being generated prior to the obtaining of the peak waveform of the Raman band by fitting a peak waveform of a Raman band corresponding to a phonon mode unique to the crystalline semiconductor film by using the Lorenz function, and
  in the lookup table, a result of the evaluation of the crystallinity of the crystalline semiconductor film which includes a crystal grain size, an existence ratio of a crystal grain, and a mobility is stored in association with the at least one of the reference peak value, the reference full-width at half maximum, and the wavelength indicating the reference peak value.

11. The non-transitory computer-readable recording medium according to claim 9,
  wherein the evaluating of the crystallinity of the semiconductor film includes determining whether or not the full-width at half maximum is in a range from $5.0 \text{ cm}^{-1}$ to $6.0 \text{ cm}^{-1}$, so as to evaluate the crystallinity of the semiconductor film.

12. The non-transitory computer-readable recording medium according to claim 9,
  wherein the semiconductor film is made of silicon, and
  the evaluating of the crystallinity of the semiconductor film includes determining whether or not a ratio of the full-width at half maximum to a full-width at half maximum of a Raman band of monocrystalline silicon is in a range from 1.5 to 1.8, so as to evaluate the crystallinity of the semiconductor film.

13. The non-transitory computer-readable recording medium according to claim 9,
  wherein the semiconductor film is made of silicon, and
  the evaluating of the crystallinity of the semiconductor film includes determining whether or not a difference between the full-width at half maximum and a full-width at half maximum of a Raman band of the monocrystalline silicon is in a range from $1.8 \text{ cm}^1$ to $2.4 \text{ cm}^1$, so as to evaluate the crystallinity of the semiconductor film.

14. The non-transitory computer-readable recording medium according to claim 9,
  wherein the evaluating of the crystallinity of the semiconductor film includes determining whether or not a ratio of the peak value to a full-width at half maximum of a Raman band of crystalline silicon is in a range from 0.1 to 0.2, so as to evaluate the crystallinity of the semiconductor film.

15. A crystallinity evaluation method of evaluating crystallinity of a semiconductor film formed above a substrate, the crystallinity evaluation method comprising:
obtaining a peak waveform of a Raman band in a Raman spectrum of the semiconductor film using Raman spectrometry, the Raman band corresponding to a phonon mode unique to the semiconductor film, the peak waveform being a waveform of a wavelength range having a peak of the Raman band;
generating a waveform by fitting the obtained peak waveform of the Raman band by using a Raman spectrum function described by a Lorenz function based on the peak waveform, the waveform being a waveform fit by the Raman spectrum function;
obtaining at least one of a peak value, a full-width at half maximum, and a wavelength indicating the peak value regarding the generated waveform; and
evaluating crystallinity of the semiconductor film based on the at least one of the peak value, the full-width at half maximum, and the wavelength indicating the peak value,
wherein the generating of the waveform includes:
generating a Raman peak waveform analysis model expressed by Equation A, where $Ic(\omega)$ denotes a Raman band of a crystalline silicon component, $I\mu c(\omega)$ denotes a Raman band of a microcrystalline silicon component, $Ia(\omega)$ denotes a Raman band of an amorphous silicon component, $\sigma_c$ denotes a volume fraction of the crystalline silicon component, $\sigma_{mc}$ denotes a volume fraction of the microcrystalline silicon component, and $\sigma_a$ denotes a volume fraction of the amorphous silicon component; and
describing each of the Raman band of the crystalline silicon component, the Raman band of the microcrystalline silicon component, and the Raman band of the amorphous silicon component, by using the Raman spectrum function as expressed by Equations B and C, where Lc denotes a phonon coherence length, a denotes a lattice constant, $\Gamma_0$ denotes a full-width at half maximum of a Raman peak of a monocrystalline semiconductor, and C denotes a normalized constant, $$I(\omega) = \sigma_a Ia(\omega) + \sigma_{mc} I\mu c(\omega) + \sigma_c Ic(\omega) \quad \text{(Equation A)}$$

$$I(\omega) = C \int_0^{2\pi} d\varphi \int_{-\pi}^{\pi} \sin\theta \, d\theta \int_0^1 \left[ \frac{\exp\left(-\frac{q^2 Lc^2}{4a}\right)}{[\omega - \omega(q)]^2 + \left(\frac{\Gamma_0}{2}\right)^2} \right] q^2 \, dq \quad \text{(Equation B)}$$

where $$\sigma_a + \sigma_{mc} + \sigma_c = 1 \quad \text{(Equation C)}.$$

16. The crystallinity evaluation method according to claim 15, further comprising:
performing, with a spectrometer, the Raman spectrometry on the semiconductor film to obtain the Raman spectrum of the semiconductor film.

17. A crystallinity evaluation device that evaluates crystallinity of a semiconductor film formed above a substrate, the crystallinity evaluation device comprising:
a processor; and
a memory including instructions that, when executed by the processor, cause the processor to perform operations including:
obtaining a peak waveform of a Raman band in a Raman spectrum of the semiconductor film using Raman spectrometry, the Raman band corresponding to a phonon mode unique to the semiconductor film, the peak waveform being a waveform of a wavelength range having a peak of the Raman band;
generating a first waveform by fitting the obtained peak waveform of the Raman band by using a Gauss function, the first waveform being a waveform fit by the Gauss function;
extracting a peak value of the first waveform;
generating a second waveform by fitting the obtained peak waveform of the Raman band by using a Lorenz function based on the extracted peak value, the second waveform being a waveform fit by the Lorenz function;
obtaining at least one of a peak value, a full-width at half maximum, and a wavelength indicating the peak value regarding the generated second waveform; and
evaluating crystallinity of the semiconductor film based on the at least one of the peak value, the full-width at half maximum, and the wavelength indicating the peak value.

18. The crystallinity evaluation device according to claim 17, further comprising:
a spectrometer that performs the Raman spectrometry on the semiconductor film to obtain the Raman spectrum of the semiconductor film.

19. A non-transitory computer-readable recording medium including executable instructions for evaluating crystallinity of a semiconductor film formed above a substrate, the executable instructions, when executed by a computer, causing the computer to perform operations to output a result of the evaluating of the crystallinity of the semiconductor film, the operations comprising:
obtaining a peak waveform of a Raman band in a Raman spectrum of the semiconductor film using Raman spectrometry, the Raman band corresponding to a phonon mode unique to the semiconductor film, the peak waveform being a waveform of a wavelength range having a peak of the Raman band;
generating a waveform by fitting the obtained peak waveform of the Raman band by using a Raman spectrum function described by a Lorenz function based on the peak waveform, the waveform being a waveform fit by the Raman spectrum function;
obtaining at least one of a peak value, a full-width at half maximum, and a wavelength indicating the peak value regarding the generated waveform; and
evaluating crystallinity of the semiconductor film based on the at least one of the peak value, the full-width at half maximum, and the wavelength indicating the peak value,
wherein the generating of the waveform includes:
generating a Raman peak waveform analysis model expressed by Equation A, where $Ic(\omega)$ denotes a Raman band of a crystalline silicon component, $I\mu c(\omega)$ denotes a Raman band of a microcrystalline silicon component, $Ia(\omega)$ denotes a Raman band of an amorphous silicon component, $\sigma_c$ denotes a volume fraction of the crystalline silicon component, $\sigma_{mc}$ denotes a volume fraction of the microcrystalline silicon component, and $\sigma_a$ denotes a volume fraction of the amorphous silicon component; and
describing each of the Raman band of the crystalline silicon component, the Raman band of the microcrystalline silicon component, and the Raman band of the amorphous silicon component, by using the Raman spectrum function as expressed by Equations B and C, where Lc denotes a phonon coherence length, a denotes a lattice constant, $\Gamma_0$ denotes a full-width at half maximum of a Raman peak of a monocrystalline semiconductor, and C denotes a normalized constant, $$I(\omega) = \sigma_a Ia(\omega) + \sigma_{mc} I\mu c(\omega) + \sigma_c Ic(\omega) \quad \text{(Equation A)}$$

$$I(\omega) = C \int_0^{2\pi} d\varphi \int_{-\pi}^{\pi} \sin\theta \, d\theta \int_0^1 \left[ \frac{\exp\left(-\frac{q^2 Lc^2}{4a}\right)}{[\omega - \omega(q)]^2 + \left(\frac{\Gamma_0}{2}\right)^2} \right] q^2 \, dq \quad \text{(Equation B)}$$

where $$\sigma_a + \sigma_{mc} + \sigma_c = 1 \quad \text{(Equation C)}.$$

* * * * *